(12) United States Patent
Tahmasian

(10) Patent No.: US 11,738,202 B2
(45) Date of Patent: Aug. 29, 2023

(54) MEDICAL DEVICE APPLICATION FOR AN EXTERNAL DEVICE USING DATA LOGGED AT AN IMPLANTABLE MEDICAL DEVICE

(71) Applicant: Boston Scientific Neuromodulation Corporation, Valencia, CA (US)

(72) Inventor: Samuel Tahmasian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 146 days.

(21) Appl. No.: 17/239,269

(22) Filed: Apr. 23, 2021

(65) Prior Publication Data

US 2021/0236830 A1  Aug. 5, 2021

Related U.S. Application Data

(60) Continuation of application No. 15/996,010, filed on Jun. 1, 2018, now Pat. No. 11,000,688, which is a
(Continued)

(51) Int. Cl.
*A61N 1/37* (2006.01)
*A61N 1/372* (2006.01)
(Continued)

(52) U.S. Cl.
CPC ..... *A61N 1/37247* (2013.01); *A61N 1/36132* (2013.01); *A61N 1/36146* (2013.01);
(Continued)

(58) Field of Classification Search
CPC . A61N 1/3787; A61N 1/37247; A61N 1/3708
See application file for complete search history.

(56) References Cited

U.S. PATENT DOCUMENTS 5,391,193 A   2/1995   Thompson
5,941,906 A   8/1999   Barreras, Sr. et al.
(Continued)

OTHER PUBLICATIONS

Medtronic, Inc.; "RestoreSensor Neurostimulator—The Choice of Continuous Motion"; May 2011; p. 1-3; Medtronic International Trading Sárl; Tolochenaz.
(Continued)

*Primary Examiner* — Eric D. Bertram
(74) *Attorney, Agent, or Firm* — Lewis & Reese, PLLC

(57) ABSTRACT

A Medical Device Application (MDA) is disclosed for an external device (e.g., a cell phone) that can communicate with an Implantable Medical Device (IMD). The MDA receives data logged in the IMD, processes that data in manners reviewable by an IMD patient, and that can control the IMD based on such processed data. The MDA can use the logged data to adjust IMD therapy based on patient activity or posture, and allows a patient to learn optimal therapy settings for particular activities. The MDA can also use the logged data to allow a patient to review details about IMD battery performance, whether such battery is primary or rechargeable, and to control stimulation parameters based on that performance. The MDA also allows a patient to enter medicine dose information, to review the relationship between medicinal therapy and IMD therapy, and to adjust IMD therapy based on the dosing information.

8 Claims, 15 Drawing Sheets

Related U.S. Application Data division of application No. 15/253,362, filed on Aug. 31, 2016, now Pat. No. 10,004,909, which is a continuation of application No. 14/476,703, filed on Sep. 3, 2014, now Pat. No. 9,433,796.

(60) Provisional application No. 61/873,314, filed on Sep. 3, 2013.

(51) Int. Cl.
*A61N 1/378* (2006.01)
*A61N 1/365* (2006.01)
*A61N 1/36* (2006.01)
*H01M 6/50* (2006.01)
G01R 31/392 (2019.01)
G01R 31/3835 (2019.01)

(52) U.S. Cl.
CPC ..... *A61N 1/36535* (2013.01); *A61N 1/36542* (2013.01); *A61N 1/3787* (2013.01); *H01M 6/505* (2013.01); *A61N 1/36071* (2013.01); *A61N 1/36157* (2013.01); *A61N 1/3708* (2013.01); *G01R 31/3835* (2019.01); *G01R 31/392* (2019.01)

(56) References Cited

U.S. PATENT DOCUMENTS

| | | | |
|---|---|---|---|
| 6,035,050 A | 3/2000 | Weinfurtner et al. | |
| 6,185,461 B1 | 2/2001 | Er | |
| 7,177,690 B2 * | 2/2007 | Woods | A61N 1/3787 |
| | | | 607/33 |
| 7,469,161 B1 | 12/2008 | Gandhi et al. | |
| 7,620,452 B1 | 11/2009 | Russie | |
| 7,974,689 B2 | 7/2011 | Volpe et al. | |
| 8,065,019 B2 | 11/2011 | Mamfeldt et al. | |
| 8,193,766 B2 * | 6/2012 | Rondoni | A61N 1/3787 |
| | | | 320/108 |
| 8,214,164 B2 | 7/2012 | Gandhi et al. | |
| 8,498,716 B2 | 7/2013 | Chen et al. | |
| 8,585,604 B2 * | 11/2013 | Bennett | G16H 50/20 |
| | | | 600/485 |
| 8,676,318 B2 | 3/2014 | Carbunaru et al. | |
| 9,101,770 B2 | 8/2015 | Arcot-Krishnamurthy et al. | |
| 9,968,734 B2 | 5/2018 | Burke et al. | |
| 2003/0059073 A1 | 3/2003 | Bren et al. | |
| 2005/0060001 A1 | 3/2005 | Singhal et al. | |
| 2005/0065553 A1 | 3/2005 | Ben Ezra et al. | |
| 2008/0058872 A1 | 3/2008 | Brockway et al. | |
| 2008/0103546 A1 | 5/2008 | Patel | |
| 2009/0069861 A1 | 3/2009 | Gandhi et al. | |
| 2009/0112291 A1 | 4/2009 | Wahlstrand et al. | |
| 2009/0276015 A1 * | 11/2009 | Rondoni | A61N 1/3787 |
| | | | 607/61 |
| 2009/0299156 A1 | 12/2009 | Simpson et al. | |
| 2010/0305663 A1 | 12/2010 | Aghassian | |
| 2011/0071597 A1 | 3/2011 | Aghassian | |
| 2011/0105955 A1 | 5/2011 | Yudovsky et al. | |
| 2011/0106213 A1 * | 5/2011 | Davis | G16Z 99/00 |
| | | | 607/59 |
| 2011/0178576 A1 | 7/2011 | Aghassian | |
| 2012/0215285 A1 | 8/2012 | Tahmasian et al. | |
| 2012/0265266 A1 | 10/2012 | Colbom | |
| 2013/0096650 A1 | 4/2013 | Aghassian | |
| 2013/0172774 A1 * | 7/2013 | Crowder | A61B 5/24 |
| | | | 600/300 |
| 2013/0184794 A1 | 7/2013 | Feldman et al. | |
| 2013/0289661 A1 | 10/2013 | Griffith et al. | |
| 2014/0100486 A1 | 4/2014 | Alberts | |
| 2014/0163638 A1 | 6/2014 | Mamfeldt et al. | |
| 2014/0257427 A1 | 9/2014 | Mamfeldt | |
| 2014/0358194 A1 | 12/2014 | Vansickle et al. | |

OTHER PUBLICATIONS

"MSP430 Ultra-Low-Power Microcontrollers," Texas Instruments, Inc. (2014) http://www.ti.com/lit/sg/slab034y/slab034y.pdf.

* cited by examiner

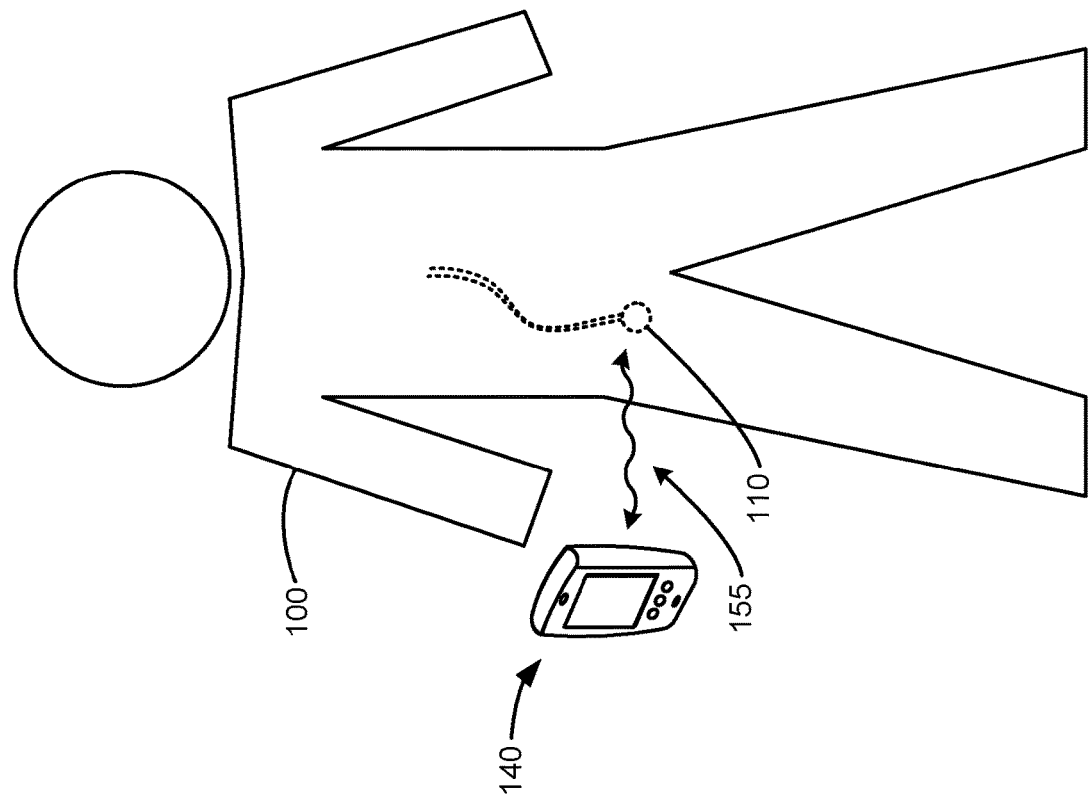
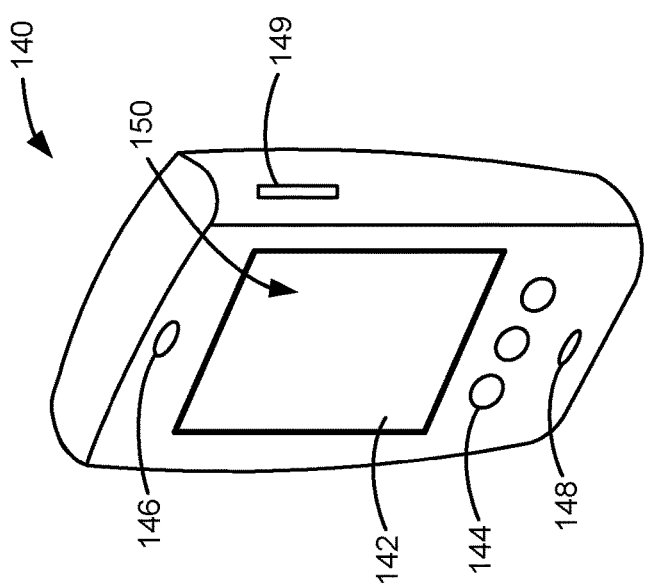
*Figure 3B*
*Figure 3A*

| | Stimulation parameters | Activity Amplitude (A) | Electrode impedance Fingerprint (FP) | IPG battery Voltage (Vbat) | IPG battery charge current (Ibat) |
|---|---|---|---|---|---|
| t1 | I1; f1; pw1; E +/− | A1 | FP1 | Vbat1 | x |
| t2 | I2; f2; pw2; E +/− | A2 | FP2 | Vbat2 | x |
| t3 | I3; f3; pw3; E +/− | A3 | FP3 | Vbat3 | x |
| t4 | I4; f4; pw4; E +/− | A4 | FP4 | Vbat4 | x |
| t5 | I5; f5; pw5; E +/− | A5 | FP5 | Vbat5 | Ibat5 ⎫ charging |
| t6 | I6; f6; pw6; E +/− | A6 | FP6 | Vbat6 | Ibat6 ⎭ |
| t7 | I7; f7; pw7; E +/− | A7 | FP7 | Vbat7 | x |
| t8 | I8; f8; pw8; E +/− | A8 | FP8 | Vbat8 | x |
| ••• | | | | | |
| t22 | I22; f22; pw22; E +/− | A22 | FP22 | Vbat22 | x |
| t23 | I23; f23; pw23; E +/− | A23 | FP23 | Vbat23 | Ibat23 ⎫ charging |
| t24 | I24; f24; pw24; E +/− | A24 | FP24 | Vbat24 | Ibat24 |
| t25 | I25; f25; pw25; E +/− | A25 | FP25 | Vbat25 | Ibat25 ⎭ |
| t26 | I26; f26; pw26; E +/− | A26 | FP26 | Vbat26 | x |
| t27 | I27; f27; pw27; E +/− | A27 | FP27 | Vbat27 | x |
| ••• | | | | | |

IPG data log 220

*Figure 7A*

MEDICAL DEVICE APPLICATION FOR AN EXTERNAL DEVICE USING DATA LOGGED AT AN IMPLANTABLE MEDICAL DEVICE

CROSS-REFERENCE TO RELATED APPLICATIONS

This application is a continuation of U.S. application Ser. No. 15/996,010, filed Jun. 1, 2018 (now U.S. Pat. No. 11,000,688), which is a divisional of U.S. application Ser. No. 15/253,362, filed Aug. 31, 2016 (now U.S. Pat. No. 10,004,909), which is a continuation of U.S. application Ser. No. 14/476,703, filed Sep. 3, 2014 (now U.S. Pat. No. 9,433,796), which is a non-provisional of U.S. Provisional Patent Application Ser. No. 61/873,314, filed Sep. 3, 2013. Priority is claimed to these applications, and they are incorporated herein by reference in their entireties.

FIELD OF THE INVENTION

The present invention relates generally to implantable medical device systems, and more particularly to mobile external devices to be used in implantable medical device systems.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators (SCS) to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within an SCS system, such as that disclosed in U.S. Pat. No. 6,516,227. However, the present invention may find applicability with any implantable medical device (IMD) or in any implantable medical device system.

As shown in FIG. 1, an SCS system typically includes an Implantable Pulse Generator (IPG) 10, which includes a biocompatible device case 12 formed of titanium, for example. The case 12 typically holds the circuitry and battery 14 necessary for the IPG to function. The IPG 10 is coupled to electrodes 16 via one or more electrode leads 18 (two of which are shown). The electrodes 16 are coupled to the IPG 10 at one or more lead connectors 20 fixed in a header 22, which can comprise an epoxy for example. In the illustrated embodiment, there are sixteen electrodes, although the number of leads and electrodes is application specific and therefore can vary. In an SCS application, two electrode leads 18 are typically implanted on the right and left side of the dura within the patient's spinal cord. The proximal ends of the leads 18 are then tunneled through the patient's tissue 60 (FIG. 2B) to a distant location, such as the buttocks, where the IPG case 12 is implanted, at which point the proximal ends are coupled to the lead connector(s) 20.

FIG. 2A shows a front view of an external controller 40 for communicating with the IPG 10, and FIG. 2B shows the external controller 40 and IPG 10 in cross section. Two coils (antennas) are generally present in the IPG 10: a telemetry coil 30 used to transmit/receive data via a bi-directional wireless communications link 55 to/from the external controller 40; and a charging coil 32 for recharging the IPG's rechargeable battery 14 using an external charger (not shown), which may also be incorporated with the external controller 40. Battery 14 may also be a non-rechargeable primary battery 14, in which case charging coil 32 would not be necessary. The coils 30 and 32 and other components necessary for IPG operation are electrically coupled to a circuit board 34. For example, an accelerometer 36 may be included within the IPG 10 to monitor patient movement or other forces. The telemetry coil 30 can be mounted within the header 22 of the IPG 10, or can be located within the case 12 as shown. The telemetry coil 30 can be coupled to telemetry circuitry 38 to modulate and demodulate a serial string of data bits sent to or received from the external controller 40. IPG 10 would also include main control circuitry, such as a microcontroller 230 (described later with reference to FIG. 7B).

The external controller 40, such as a hand-held programmer or a clinician's programmer, is used to send or adjust the stimulation parameters the IPG 10 will provide to the patient (such as which electrodes 16 are active, whether such electrodes sink and source current, and the pulse width, frequency, and intensity of pulses formed at the electrodes, etc.). The external controller 40 can also act as a receiver of data from the IPG 10, such as various data reporting on the IPG's status and the level of the IPG 10's battery 14. The external controller 40 is itself powered by a battery 42, but could also be powered by plugging it into a wall outlet for example. A Graphical User Interface (GUI) similar to that used for a cell phone is provided to operate the external controller 40, including buttons 44 and a display 46. The external controller 40 also includes a data telemetry coil 48. These and other components 45 necessary for IPG operation are electrically coupled in the external controller 40 to a circuit board 47.

Wireless data transfer between the IPG 10 and the external controller 40 typically takes place via magnetic inductive coupling between coils 30 and 48, each of which can act as the transmitter or the receiver to enable two-way communication between the two devices. A Frequency Shift Keying (FSK) protocol can be used to send data between the two coils 30 and 48 via link 55. Although use of an FSK protocol along link 55 is discussed below, use of this protocol is not universal, and other protocols employing different forms of modulation can be used to communicate between an external controller and an IPG, as one skilled in the art understands. Telemetry of data can occur transcutaneously though a patient's tissue 60.

Historically, external medical devices such as external controller 40 have been built by the manufacturer of the IPGs, and thus such external devices are generally dedicated to only communicate with such IPGs. The inventor has realized that there are many commercial mobile devices, such as multi-function mobile cell phones and tablets, that have the necessary configurable hardware and software to communicate using short-range protocols and thus may function as an external controller for an IPG or other implantable medical device. Using such mobile devices as external controllers for an implantable medical device would benefit both manufacturers and end users: manufacturers would not need to build dedicated external controllers that end users must buy, and end users could control their IPGs without the inconvenience of having to carry additional custom external controllers.

A Medical Device Application (MDA) for use on a mobile device, or other suitably-powerful external device capable of communicating with an IPG or other implantable medical device, is disclosed with improved functionality, which leverages the increased processing power and memory of such mobile devices to improve patient communications with his implant; to improve patient control of his implant; and to provide a patient more-detailed information concerning operation of his implant.

BRIEF DESCRIPTION OF THE DRAWINGS

FIG. 3A shows a mobile device in accordance with an embodiment of the present invention, and FIG. 3B shows the mobile device in wireless communication with an IPG.

FIG. 7A shows an example of an IPG data log useable by the MDA 170.

DETAILED DESCRIPTION

Figure 1:
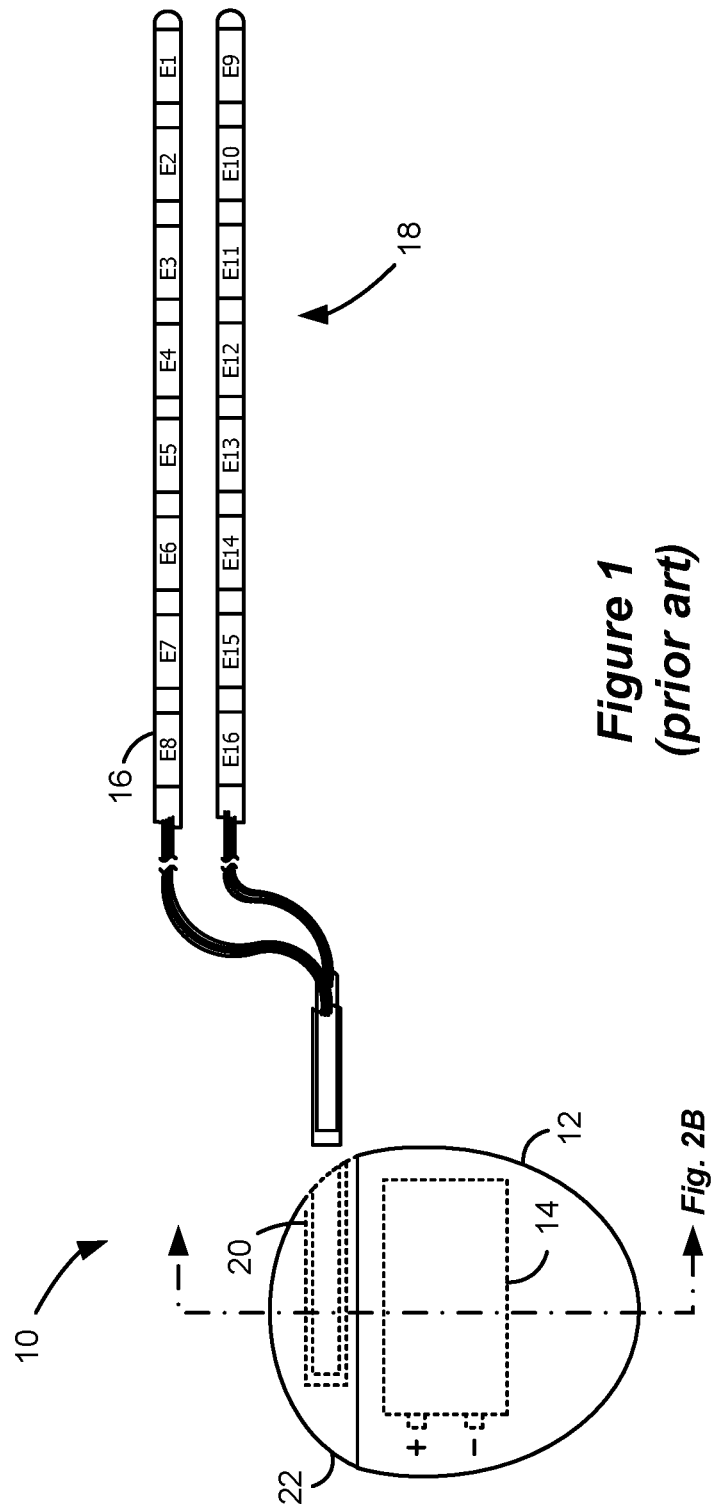
FIG. 1 shows an implantable pulse generator (IPG) in accordance with the prior art.

FIG. 3A shows a mobile device 140, and FIG. 3B shows the mobile device 140 in communication with an IPG 110 implanted in a patient 100 via a bi-directional communication link 155. Communication link 155 may or may not differ from link 55 established by a traditional dedicated external controller 40 (FIGS. 2A and 2B), and the particulars of link 155 may be dictated by the type of short-range communication means used in the mobile device 140 and in the IPG 110. IPG 110 may be the same as IPG 10 discussed earlier, or may include modifications consistent with operation of the invention, as described in further detail later. The mobile device 140 may be a commercial, multipurpose, consumer device, such as a cell phone, tablet, personal data assistant, laptop or notebook computer, or like devices-essentially any mobile, hand-holdable device capable of functioning as an external controller for an implantable medical device. Examples include the Apple iPhone or iPad, Microsoft Surface, Nokia Lumia devices, Samsung Galaxy devices, or Google Android devices, for example.

Among other components and circuitry which will be described in further detail later, the mobile device 140 has a Graphical User Interface (GUI) 150. For example, mobile device 140 may have a display 142 for displaying information. Display 142 may also receive input from a patient if it is a touch screen that receives input from a finger or stylus. The mobile device 140 may also have buttons 144 for receiving input from the patient, a speaker 146, and a microphone 148. The mobile device 140 may have one or more external ports 149, such as a USB port for example, to connect the mobile device 140 to other devices. Although not shown, such other devices can include for example chargers for the mobile device's battery, other computer systems, memory cards, sticks, and dongles, etc.

Figure 2B:
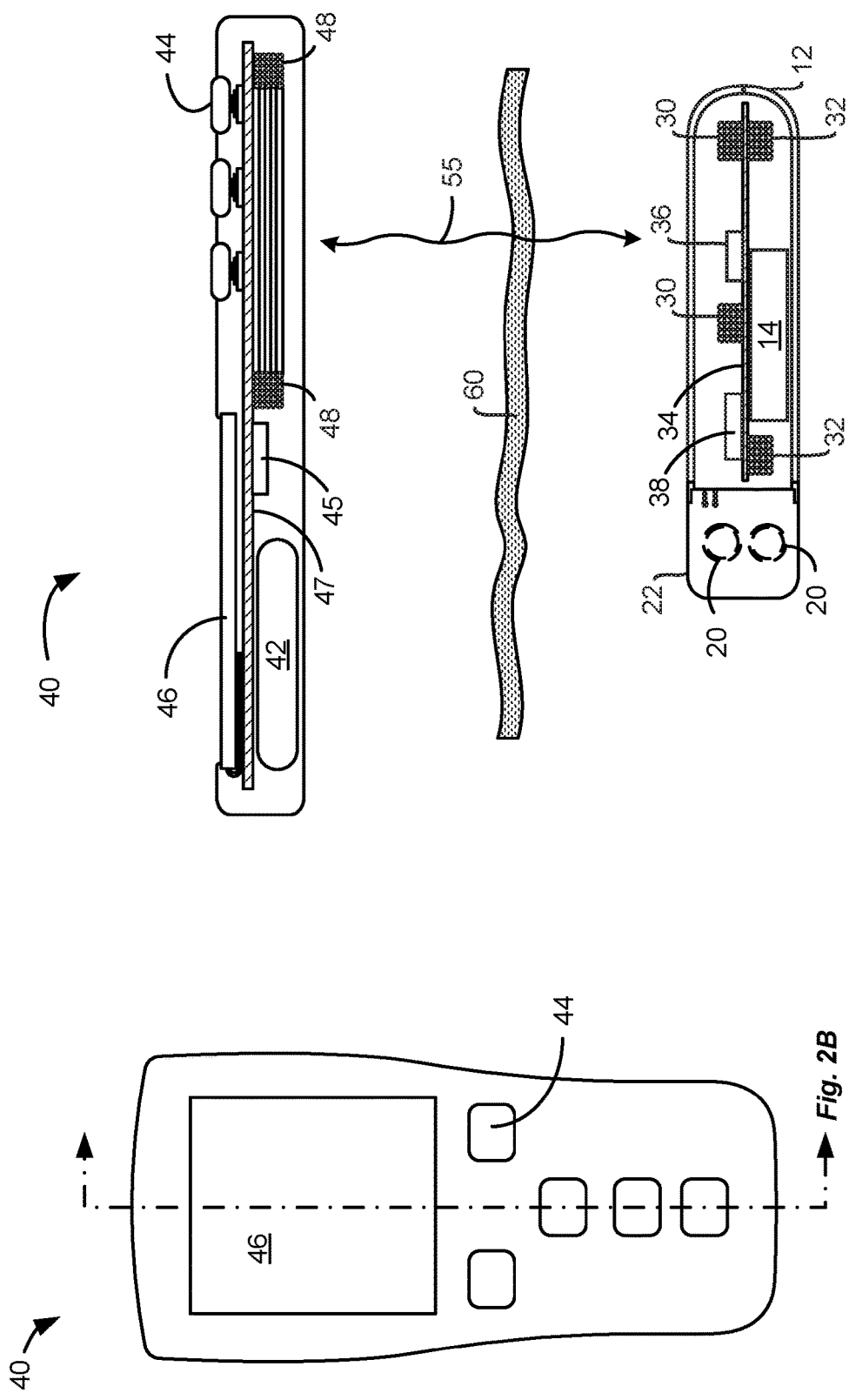
FIGS. 2A and 2B show an external controller and the manner in which it communicates with the IPG in accordance with the prior art.
Figure 2A:
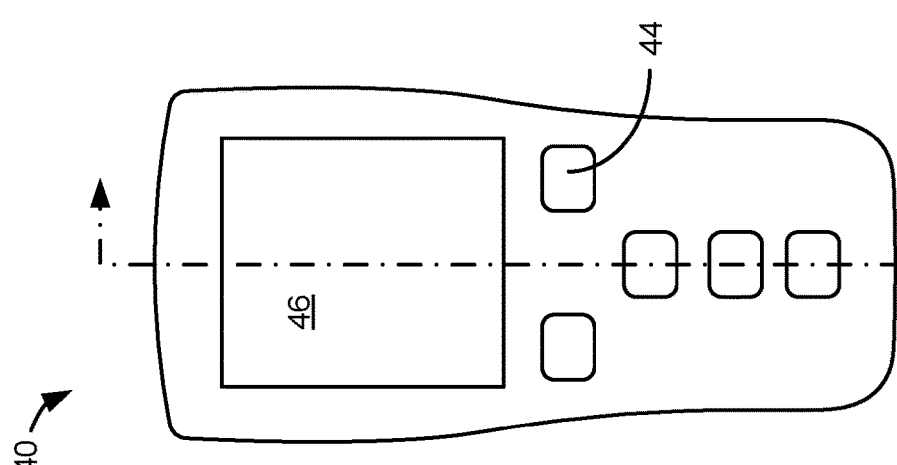

The inventor has realized that an implantable medical device such as IPG 10 (FIG. 1) typically logs copious amounts of data for various reasons. While such logged data can be retrieved from the IPG by a clinician or IPG manufacturer using special diagnostic tools, such data is typically not reviewable by a patient using a traditional external controller 40 (FIGS. 2A and 2B). This is understandable, as traditional external controllers 40 are typically relatively simple: they provide relatively simple GUIs limited to sending stimulation parameters to the IPG, and to presenting limited data from the IPG, such as IPG battery status or perhaps information indicative of IPG status. Even if other logged data in the IPG were transmitted to the external controller 40, the external controller 40 may lack the ability to process such data. Moreover, traditional external controllers 40 may also lack the memory to store significant amounts of such data transmitted from the IPG. However, a general-purpose mobile device 140 does not suffer from the same limitations.

A Medical Device Application (MDA) is thus disclosed for a mobile device or other capable external controller (hereinafter "external device") that allows for receipt of a greater variety and amount of data logged in the IPG; that can process that received data in manners reviewable by a patient; and that can control the IPG based on such processed data. In conjunction with such logged data, the MDA at the external device can preferably automatically adjust the stimulation parameters provided to the IPG based on patient activity or posture, as well as allow a patient to learn optimal stimulation parameters for particular activities. The MDA can also use the logged IPG data to allow a patient to review further details about IPG battery performance, whether such battery is primary or rechargeable, and to control stimulation parameters based on that performance if necessary. Other aspects of the MDA allow a patient to enter dosing information concerning medicines the patient is taking; to review the relationship between such medicinal therapy and stimulation therapy provided by the IPG; and to automatically adjust the stimulation parameters provided by the IPG based on dosing information.

Figure 4:
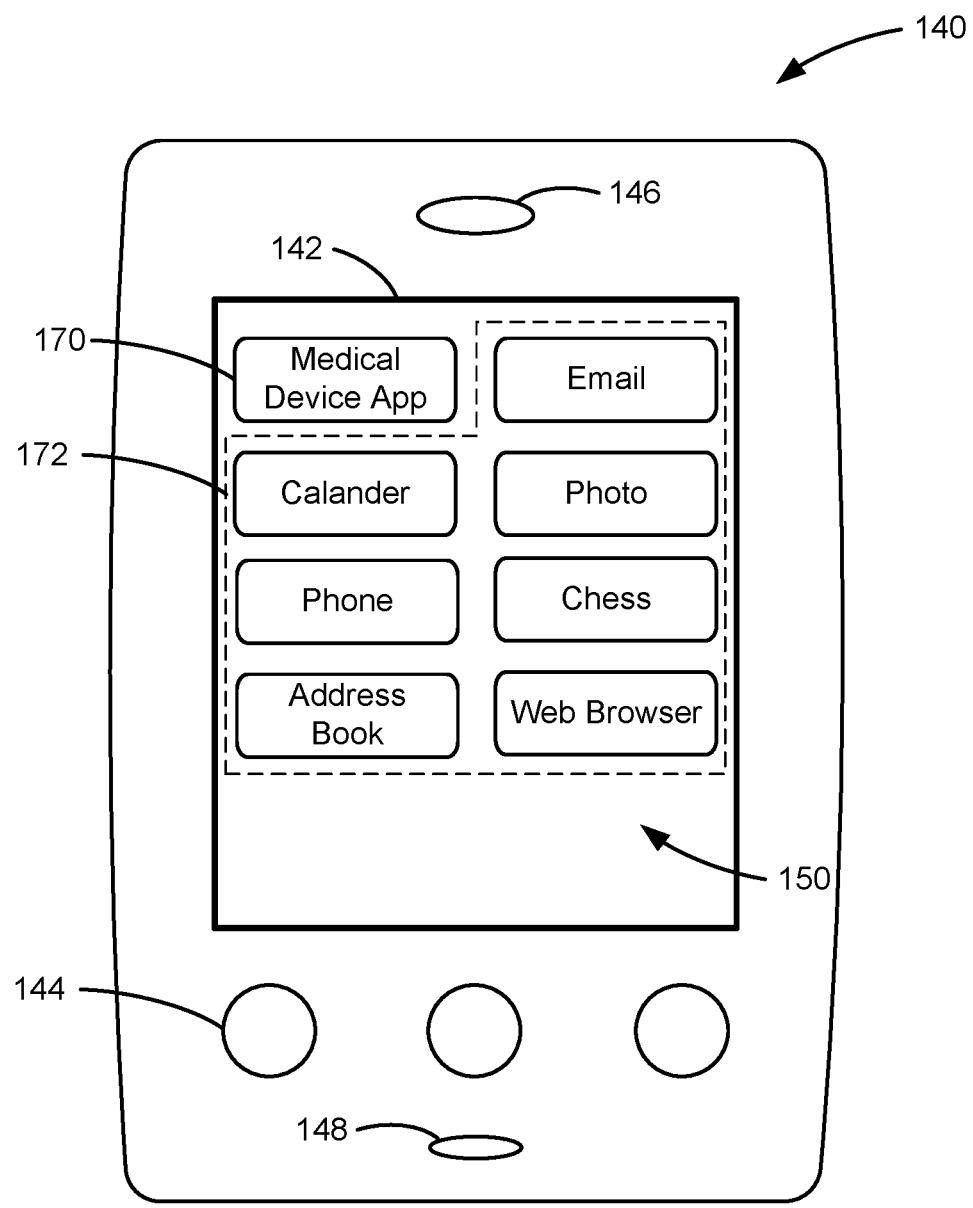
FIG. 4 shows an exemplary manner in which a Medical Device Application (MDA) can be selected on the mobile device via a mobile device Graphical User Interface (GUI).

As shown in FIG. 4, MDA 170 can be wirelessly downloaded to a patient's external device 140 by standard means (e.g., from the Internet), but may also be provided at a physical port (e.g., 149) on the external device 140, which can receive cables, or portable memory devices such as memory sticks or memory cards to load the MDA 170 into the external device 140. The MDA 170 once downloaded or loaded into the external device 140 can appear as an icon in the external device's GUI 150, and can be selected by the patient in a typical fashion, such as by touching the display 142 or buttons 144. Icons for other downloaded applications 172 that the patient can select may also be displayed. The MDA 170 can also be provided to the external device 140 in different manners.

Different types of external devices (e.g., mobile devices) comprise different hardware platforms and run different operating systems. As such, different external devices may require different MDAs 170 customized to that operating system or hardware platform. Additionally, different MDAs may be needed in light of the capabilities of the implantable medical device and the therapy it provides. For example, if the implantable medical device is an IPG, the MDA will provide a suitable GUI for communicating with that device, such as by providing options to send or adjust stimulation therapy settings. A suitable MDA 170 is likely (but not necessarily) provided to a patient by the manufacturer of the implantable medical device, although the MDA could be downloaded to the external device 140 from a number of sources, such as a manufacturer's website or an "app store" that supports applications written for the operating system of the patient's external device 140.

Figure 5:
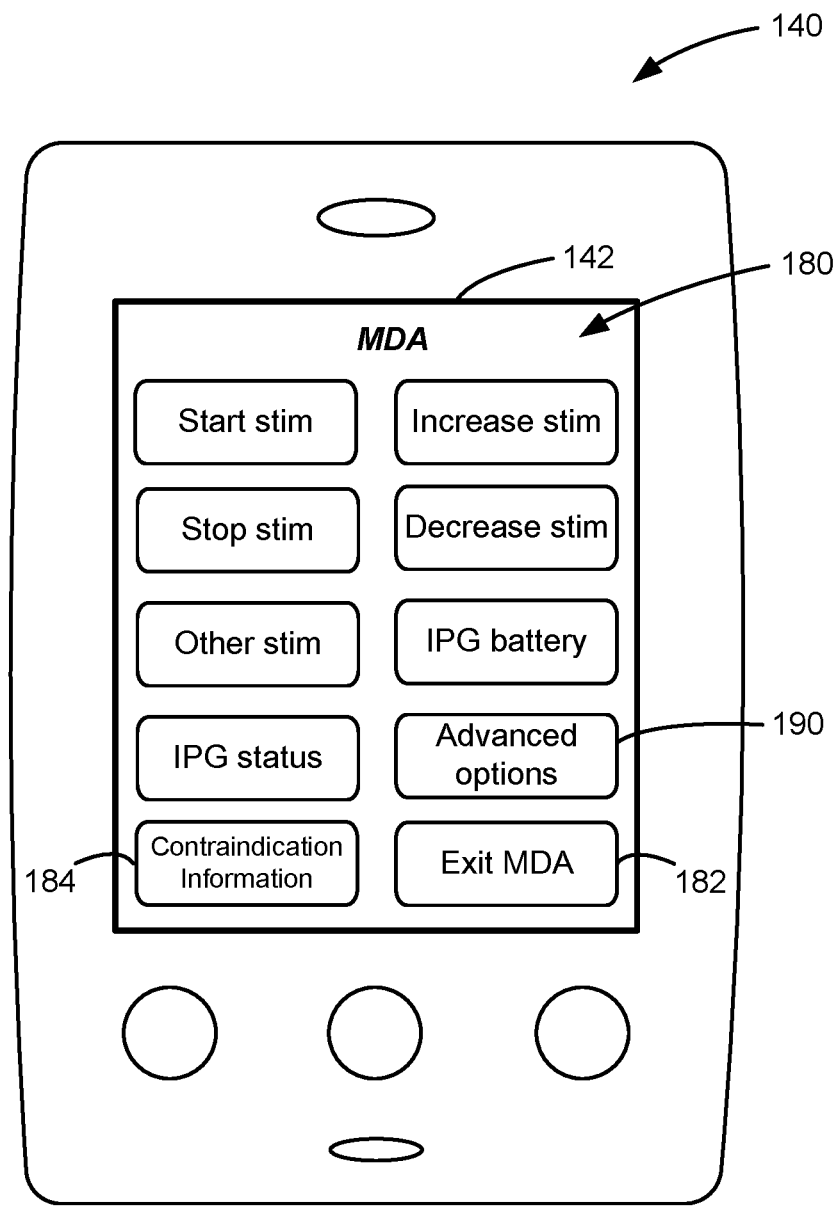
FIG. 5 shows an MDA GUI of the mobile device to enable communications between the mobile device and the IPG.

If MDA 170 is selected and executed on the external device 140, an MDA GUI 180 is presented that provides basic IPG-control functionality, as shown in FIG. 5. For example, the MDA GUI 180 may present options to start or stop stimulation; to increase or decrease the intensity of stimulation; to check the IPG's current battery status (e.g., its voltage Vbat); to change other stimulation parameters (such as active electrodes, polarity, frequency, and pulse width, etc.); or to check the IPG's status, as are typical. Such options are generally provided by the GUIs of traditional external controllers (40; FIGS. 2A and 2B) as well. An option to exit the MDA may also be provided (182), which will end the IPG communication session and return to the external device GUI 150 of FIG. 4.

MDA GUI 180 may additionally include a selectable option 184 to provide contraindication information to the patient, similar to the technique disclosed in U.S. Pat. No. 8,588,925, which is incorporated herein by reference. The '925 patent explains that "contraindication information" can be stored in a traditional dedicated external controller, such as the external controller 40 of FIGS. 2A and 2B, allowing such information to be reviewed on the external controller 40 itself, or provided from the external controller 40 (e.g., by cable, by a memory stick, wirelessly, etc.) to another computer device or system and reviewed there (such as a clinician's computer). Such "contraindication information" can comprise information that a patient or clinician might wish to review when assessing the compatibility of a given therapeutic or diagnostic technique or other activity with the patient's implant, such as: the patient or clinician's manuals for the implant system, including the manuals for the implant and any associated external devices (e.g., remote controllers or external chargers); any specific contraindicated therapeutic or diagnostic techniques or activities; contact information for the manufacturer of the implant system or its service representative; clinician contact information, for example the contact information of the clinician who implanted the implant, or another clinician having information relevant to the use of particular therapeutic or diagnostic techniques or other contraindicated or compatible activities; clinician instructions regarding therapeutic or diagnostic techniques or activities compatible with or contraindicated by the patient's implant; patient history or patient records relevant to a particular therapeutic or diagnostic techniques or activities compatible with or contraindicated by the patient's implant; etc. "Contraindication indication" can also indicate procedures or activities that are compatible with the patient's implant as well as those that are prohibited, at least to some conditional degree. Similar to the teaching of the '925 patent, contraindication information may be stored in the external device 140, and via option 184 may be shown on its display 142 or provided from the external device (e.g., wirelessly, using its short-range communication means as explained earlier) to another computer device or system (not shown).

Figure 6:
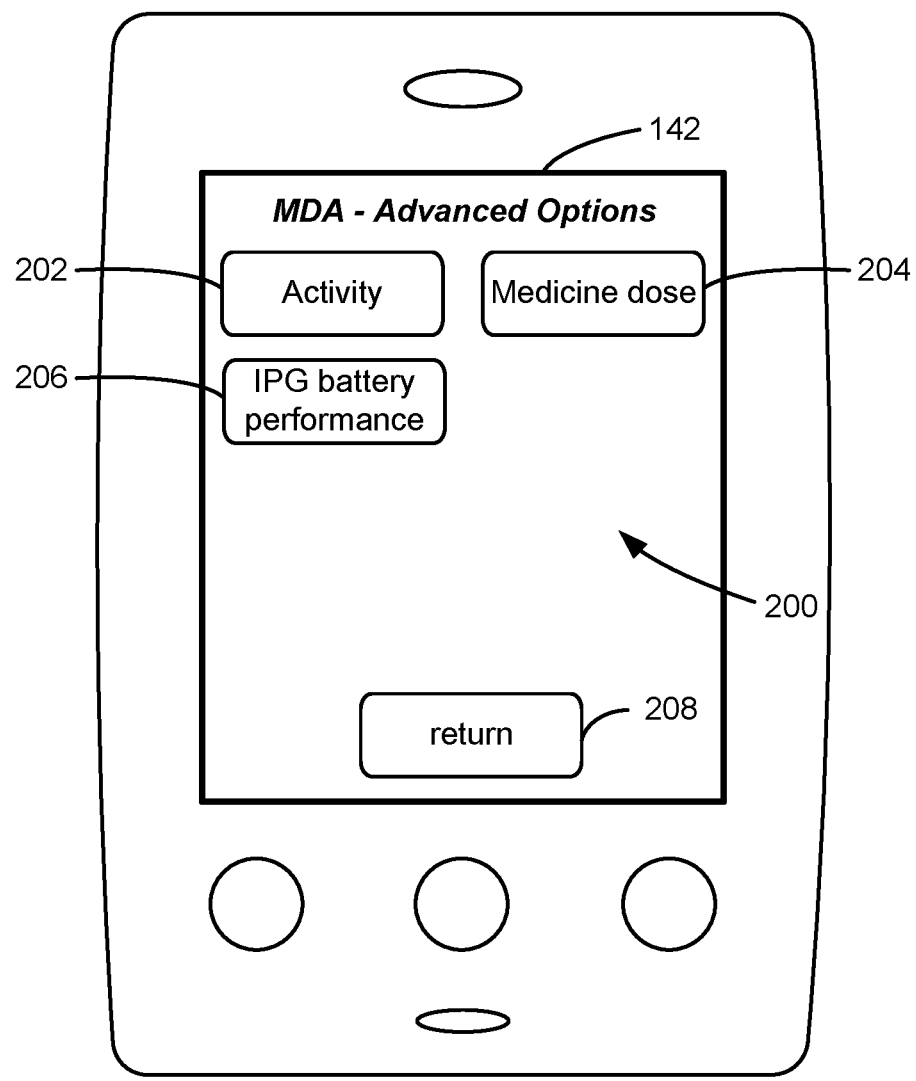
FIG. 6 shows part of the MDA GUI providing advanced options of the MDA.

Another option in the MDA GUI 180 of pertinence to the present invention is advanced options 190, which when selected takes the patient to an advanced options GUI 200 in the MDA 170 as shown in FIG. 6. Shown are three advanced options provided by the MDA 170: an activity option 202, a medicine dose option 204, and an IPG battery performance option 206, all of which are discussed below. An option to return to the previous screen 208 in the MDA 170 (i.e., to FIG. 5) may also be present.

Figure 7B:
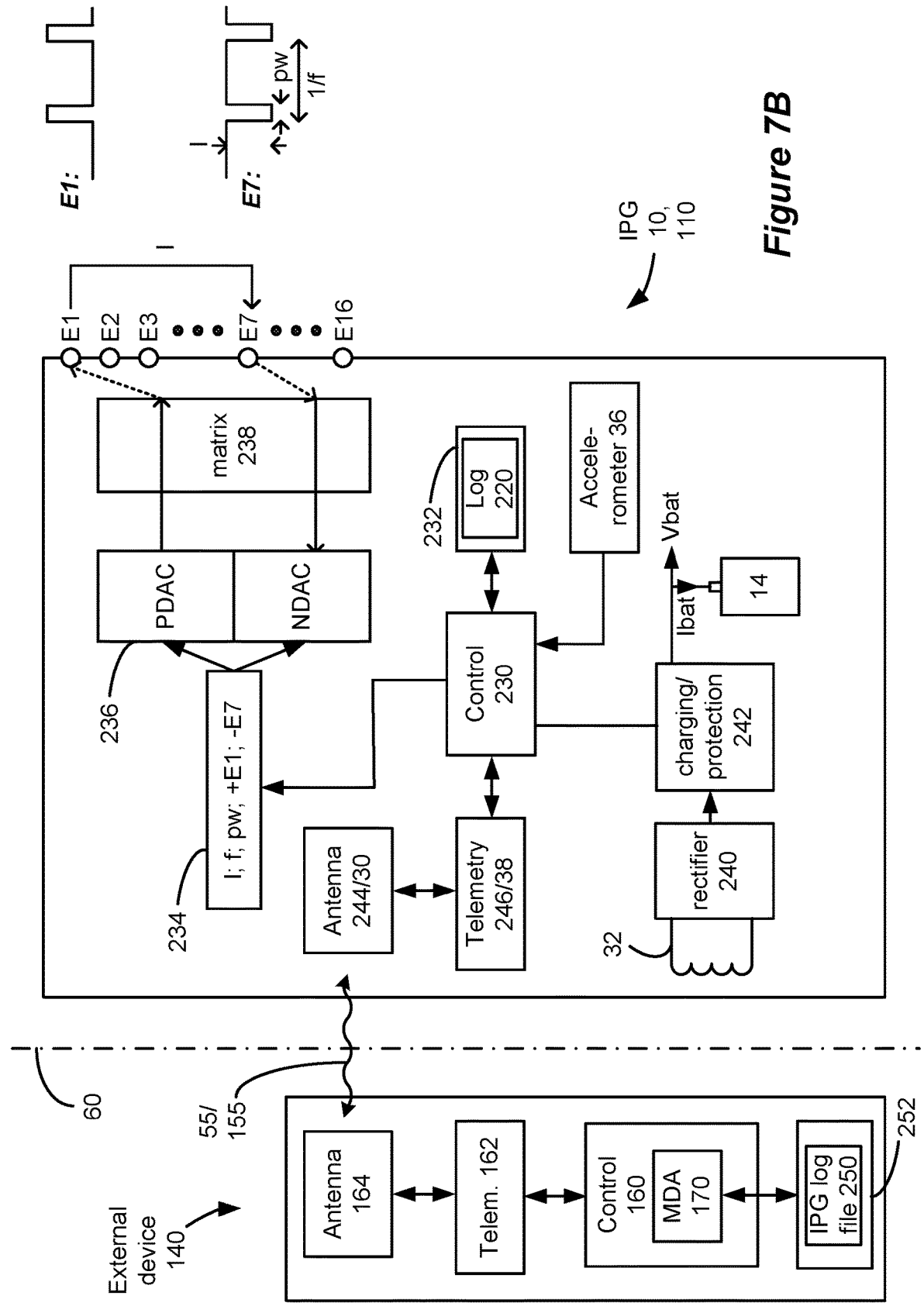
FIG. 7B shows the IPG data log in the context of other IPG circuitry.

An example of an IPG data log 220 useable by the MDA 170, and particularly by the advanced options presented in GUI 200, is shown in FIG. 7A, and IPG data log 220 is shown in the context of other IPG circuitry in FIG. 7B. While an IPG might in some embodiments keep separate logs for separate functions (e.g., a stimulation parameter log, a charging log, etc.), these are consolidated in one log 220 in FIG. 7A for ease of illustration. As shown, data is periodically logged and time stamped (t) by the IPG, which may occur at any reasonable interval. Periodic logging however is not strictly necessary, and instead data may only be logged upon the occurrence of an event in the IPG, such as a change in one of the parameters stored in the log 220. Also, not all of the illustrated parameters may be logged in 220 at every given entry, and so they can be logged at different times or on different time scales.

At each time-stamped entry, the control circuitry 230 (FIG. 7B) in the IPG (e.g., a microcontroller) logs pertinent parameters in the IPG data log 220, which may be stored in a memory 232 within or accessible by the control circuitry 230. Such parameters may include stimulation parameters such as pulse intensity (I), pulse frequency (f), pulse width (pw), active electrodes and their polarities (E1+ (anode), E7− (cathode)), which stimulation parameters are better appreciated upon review of the pulse waveforms in FIG. 7B. As shown in FIG. 7B, the control circuitry 230 in the IPG has loaded current stimulation parameters (e.g., those last listed in the IPG data log 220) to a stimulation timing channel 234. The timing channel 234 controls current generation circuitry 236 in the IPG to create the pulses as specified through the patient's tissue 60 at the active electrodes with the correct polarities. As is known, the current generation circuitry 236 can comprise one or more controllable current sources (PDAC(s)) and current sinks (NDAC(s)), which can be connected to the active electrodes (e.g., E1 and E7) by a switch matrix 238. The resulting pulses are illustrated simply in FIG. 7B. For example, they are not depicted as bi-phasic pulses and do not show provision of charge recovery during non-pulse periods, as typically occurs in an IPG. See, e.g., U.S. Patent Application Publication 2013/0184794 for further details.

Returning to FIG. 7A, further shown in the IPG data log 220 are entries related to patient activity, which are provided for example by the accelerometer 36 in the IPG discussed earlier. The data from the accelerometer 36 is illustrated as an activity amplitude (A) based on the magnitude of the forces that the accelerometer detects. Although accelerometer 36 may be able to detect force magnitudes in three directions (e.g., Ax, Ay, and Az), only a single activity amplitude (A) is shown in IPG data log 220 for simplicity. Also provided in IPG data log 220 are electrode impedance fingerprints (FP), which are useful to determining patient posture, as described in U.S. Pat. No. 9,446,243, which is incorporated herein by reference in its entirety. Parameters A and FP are collectively referred to herein as "activity parameters." The voltage of the battery 14 in the IPG (Vbat) is also measured by the IPG and stored in log 220, as is the battery charge current (Ibat), which is explained further below.

The IPG data log 220 also preferably contains data relevant to wireless charging of the battery 14 (FIGS. 1 and 2B), assuming it is a rechargeable and not a primary battery. Referring to FIG. 7B, a rechargeable battery 14 can be charged by an external charger, which is not shown but which is well known. See, e.g., U.S. Patent Application Publication 2013/0096652. An external charger creating a AC magnetic field, which is received at the IPG charging coil 32, where it is rectified 240 and used to create a battery charging current (Ibat) to charge the battery 14, perhaps under the control of battery charging and protection circuitry 242. Wireless charging in this manner only occurs from time to time as needed, and so in IPG data log 220 it is seen that Ibat is only reported during charging, which can be made known to the control circuitry 230 in the IPG via the charging and protection circuitry 242. That is generally indicative of how intensely the battery 14 is being charged, which is a function of the coupling between the external charger and the IPG. Other data indicative of battery charging intensity could be logged by the IPG in log 220 as well. If the battery 14 in the IPG is a primary battery, battery charge current data would be omitted from the log 220.

Other IPG data could be provided in log 220 as well, and likely would be logged in an IPG implementation, such as IPG mode data, error codes, etc. However, the example data in log 220 is sufficient to illustrate operation of the algorithms performed by the MDA 170 in the external device 140.

As noted earlier, the MDA 170 uses data from the IPG data log 220, and so this data is transmitted from the IPG to the external device 140 at some point during communication sessions. This can occur at different times and in different manners. In one example, when the patient executes the MDA 170 (FIG. 4) and the MDA GUI 180 appears (FIG. 5), the external device 140 may "handshake" with the IPG in a traditional fashion to establish communication link 155. In this regard, the external device 140 includes an antenna 164 and telemetry circuitry 162 compliant with short-range communications and protocols used on link 155. The IPG also includes an antenna 244 and telemetry circuitry 246 compliant with communications on link 155. Note that the IPG antenna 244 and telemetry circuitry 246 may be different from the antenna coil 30 and telemetry circuitry 38 described earlier for IPG 10, but this is not necessarily the case, particularly if the external device 140 is capable of communicating with the IPG via link 55 as discussed earlier.

After handshaking, the external device 140 can instruct the IPG via link 155/55 to upload its log 220. Alternatively, the IPG can upload the log 220 unilaterally when it recognizes that it can communicate with the external device 140. The MDA 170 may provide a message on the MDA GUI 180 to inform the patient that uploading of the log 220 is occurring, and that the patient should wait before using MDA 170 on the external device 140 to control his IPG.

Transmission of the IPG data log 220 can occur at other times during communication sessions as well. For example, the MDA 170 may cause transfer of the log 220 only when it is needed by the MDA 170, such as when any of the advanced options in GUI 200 (FIG. 6; 202, 204, or 206) are chosen. Transmission of the log 220 to the external device 140 can also occur at other convenient times during a communication session, such as when the bi-directional communication link 155/55 is established, but is not being used at the moment.

The IPG can either upload its log 220 to the external device 140 in its entirety, or may record the last entry transmitted, and begin with transmission of subsequent entries. For example, if the IPG records that it sent its log 220 up through time t11 in its last communication session with the external device 140, it may start uploading at entries starting from time t12 in a next communication session. The IPG may also clear entries at time t11 and earlier from its log 220 once they have been confirmed as received at the external device 140, which may be reasonable because the memory 232 storing the log 220 may be small given space constraints in the IPG.

As shown in FIG. 7B, the external device 140 preferably keeps all IPG log data reported to it in a file 250 accessible by the MDA 170. This IPG log file 250 can thus grow as the IPG uploads new data from log 220 from time to time during different communication sessions. Because the external device 140 has ample memory 252, storing a growing IPG log file 250 is generally not a concern for the external device 140. Alternatively, the MDA 170 may limit the size of the IPG log file 250 accordingly, such as to one year's worth of data, and delete older entries in its file. If the time base of the IPG has drifted, changed, or reset, for some reason (e.g., because its rechargeable battery 14 has depleted), the IPG can resynchronize its time base with the assistance of the external device 140 and correct the time stamps in its log 220, as disclosed in U.S. Pat. No. 8,065,019. This ensures that entries in the IPG log file 250 are properly chronologized at the external device 140. As one skilled in the art will appreciate, MDA 170 is executable by control circuitry 160 (e.g., a microcontroller) in the external device 140, and may be stored within the control circuitry (as microcode) or made accessible to the control circuitry (e.g., in memory 252).

Figure 8A:
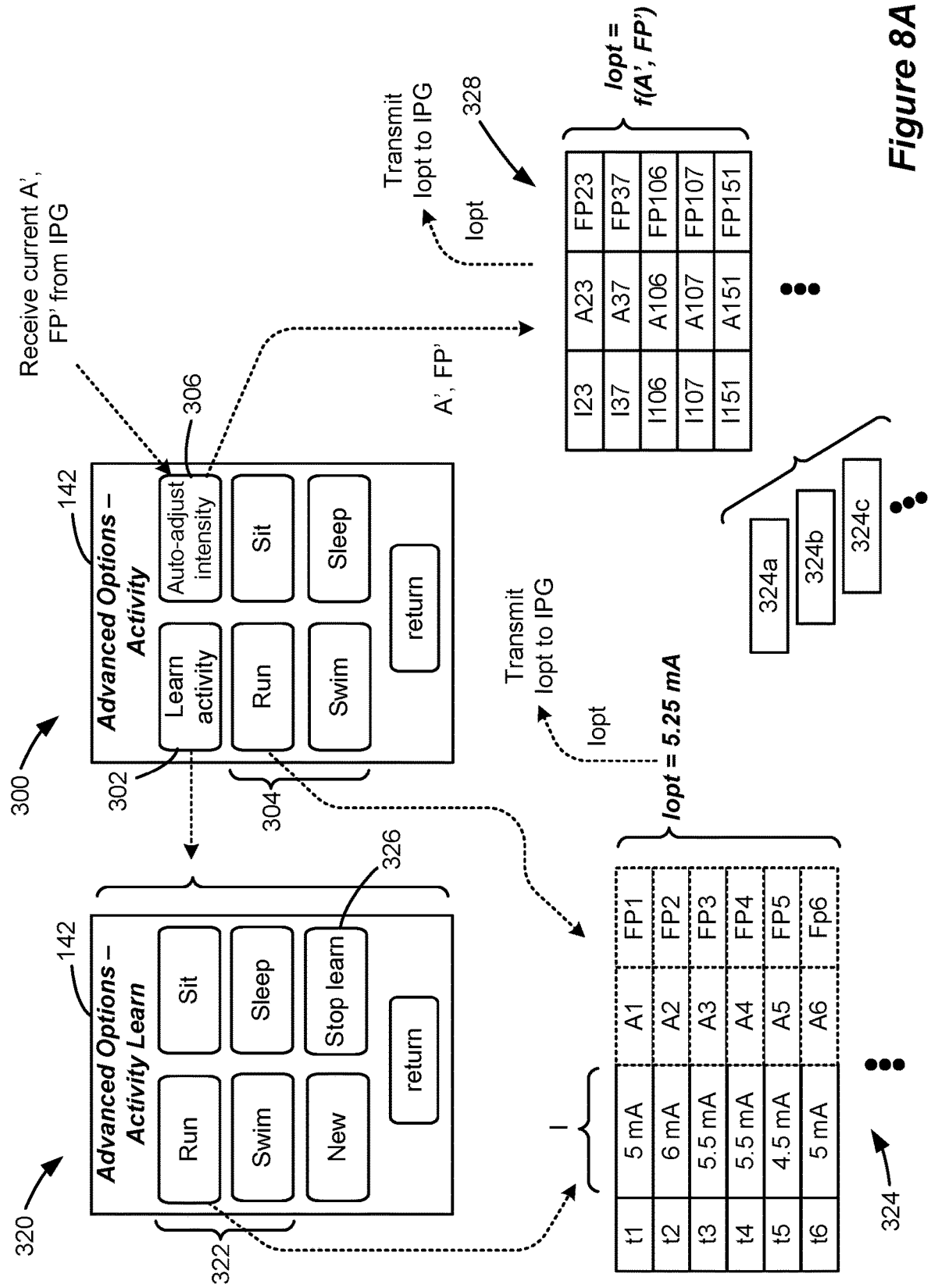
FIGS. 8A and 8B show patient activity advanced options of the MDA.

FIG. 8A illustrates the GUI 300 that appears in the MDA 170 when the "activity" advanced option 202 (FIG. 6) is selected by the patient. This option 202 is used to control one or more stimulation parameters operating in the IPG based on a particular patient activity. Only control of a single stimulation parameter-stimulation intensity (I)—is discussed here for simplicity, even though other stimulation parameters (f, pw, Ex, etc.) could be similarly controlled. Such control by the external device 140 can occur in different ways using at least some of the data in IPG log 220. As shown, the activity GUI 300 includes various activities 304 that a patient could be engaged in, such as running, sitting, swimming, sleeping, etc. When an activity 304 is selected by the patient, MDA 170 will cause the external device 140 to transmit optimal stimulation parameters for the patient and for that activity to the IPG.

Learn activity option 302 allows the MDA 170 to learn (i.e., correlate) optimal intensities for the different activities. If the patient is about to begin an activity, for example running, he can select this 302, which will take him to an activity learning GUI 320, as shown to the left in FIG. 8A. This activity learning GUI 320 provides different activities 322 that can be learned, including an option to allow the patient to enter a "new" activity not presently listed, which once entered would show on the activity GUI 300 and the activity learning GUI 320 as a selectable option.

In the following example, assume the patient selects the "run" learn activity option 322, and begins running. During learning, the MDA 170 can receive the IPG data log 220 and/or can consider information already known to the MDA 170, regarding the stimulation parameters (e.g., intensity), which the patient can change using the external device 140 as he runs to levels that are comfortable. Specifically, the MDA 170 can create an activity learning file 324, which records intensity during the activity. Activity parameters A and FP (from log 220) may also be stored in the activity learning file 324, as is useful for reasons to be explained shortly. As shown, the MDA 170 time stamps entries in the activity learning file 324. Once the patient is done running, he can select the stop learning option 326, at which point the MDA 170 will stop populating the activity learning file 324. However, the activity learning file 324 can grow in length at the MDA 170. For example, if the patient runs again tomorrow, he can again select the run learning option 322 and begin running, and the MDA 170 will continue populating the activity learning file 324, as it is beneficial to provide the MDA 170 with further data concerning this activity.

Intensity values (I) in the activity learning file 324 can come either from the MDA 170, i.e., from the external device 140, or because the external device 140 has access to the log file 250, it can also come from that file, and ultimately from the IPG (220). In this regard, MDA 170 need not directly record or receive this intensity data during the activity (even if known to the MDA 170) as it can later be procured from the IPG data log 220/log file 250 and reconciled with the activity learning file 324. That is, time stamps in the activity learning file 324 can later (e.g., after the activity) be populated with the values for I by pulling entries from the log file 250 having the same time stamps, or time stamps that are close in time. In this regard, note that activity learning file 324 may, before such reconciliation, merely comprise the time stamps or a time period denoting the starting and stopping of learning the activity.

Eventually, when enough data is present in the activity learning file 324, the MDA 170 can average the values for the intensity stored in the file 324, and create an optimal intensity (Iopt) for that activity. The MDA 170 might then also present the activity as a control option 304 on the activity GUI 300 to allow the patient to control his IPG in accordance with what was learned during the activity. For example, after learning the patient's intensity settings while running (324), and determining Iopt, selecting the run control option 304 will cause Iopt to be sent to the IPG for execution.

The auto-adjust intensity option 306 in the activity GUI 300 also controls intensity based on patient activity, but can do so without knowledge of the particular activity the patient is engaged in. The auto-adjust intensity option 306 controls the IPG based on the patient's present level of activity (A', as provided by the IPG's accelerometer 36) and posture (FP', as provided by the electrode impedance fingerprint) reported to the external device 140 from the IPG. (Prime symbols here differentiate current values x' from historical values x). Thus, when selected, the MDA 170 calls on the IPG to provide these current activity parameters A' and FP'. These activity parameters may only be sent once by the IPG, or they may be sent on a continuing basis at suitable intervals to allow the IPG to be controlled as patient activity changes.

Such auto-adjustment is facilitated by an activity history file 238. As noted above, the activity learning file(s) 324 (e.g., one per activity, or just one file 324 including associations with the activities) can additionally include activity parameters A and FP, which are ultimately included in the IPG data log 220, and eventually provided to the external device 140 as IPG data file 250. These activity file(s) 324x can then be consolidated into the activity history file 328, which associates the intensities (Ix) used by the patient with different activity parameters Ax and FPx measured at that time. Notice that the activity history file 328 need not include the time stamps (t). The MDA 170 can then receive and review the present activity parameters A' and FP' from the IPG to determine an optimal intensity (Iopt) using the activity history file 328. In a simple example, this may comprise searching the activity history file 328 for entries having values Ax and FPx that are similar to A' and FP' currently being reported by the IPG, and reviewing (e.g., averaging) the corresponding intensities (Ix) for those entries; more complicated statistics could also be used. Once determined, the value for Iopt can be transmitted to the IPG where it is executed. If patient activity doesn't remain constant (e.g., if the patient begins running faster, or starts a new activity such as swimming), new current values for A' and FP' are received from the IPG, and Iopt is updated and transmitted to the IPG after consulting the activity history file 328. In effect, the auto-adjust intensity option 306 provides Iopt to the IPG by consulting the activity history file 328 (or simply by pulling the relevant information from the activity learning file(s) 324) and determining an intensity that was used previously by the patient for a similar activity level, and which was presumably suitable for the patient at that earlier time.

Review of fingerprint data (FP) is particularly useful with the auto-adjust intensity option 306, because not all patient activities can be differentiated based on movement alone. For example, both sitting and sleeping involve little patient movement, and so activity amplitude A (likely near zero during these activities) may be of little use. Yet, the different postures provided by these activities may well result in different fingerprints in the IPG that warrant different stimulation parameters, as explained in the '243 Patent incorporated above.

Some activities may have natural or desired stages (sub-activities) where the optimal patient stimulation may be different for each sub-activity. The activity of running, for example, may comprise three sub-activities: warm up, active running, and cool down. Learning the optimal stimulation for each sub-activity allows the MDA 170 to transmit updated stimulation parameters to the IPG when those each sub-activities occur.

Figure 8B:
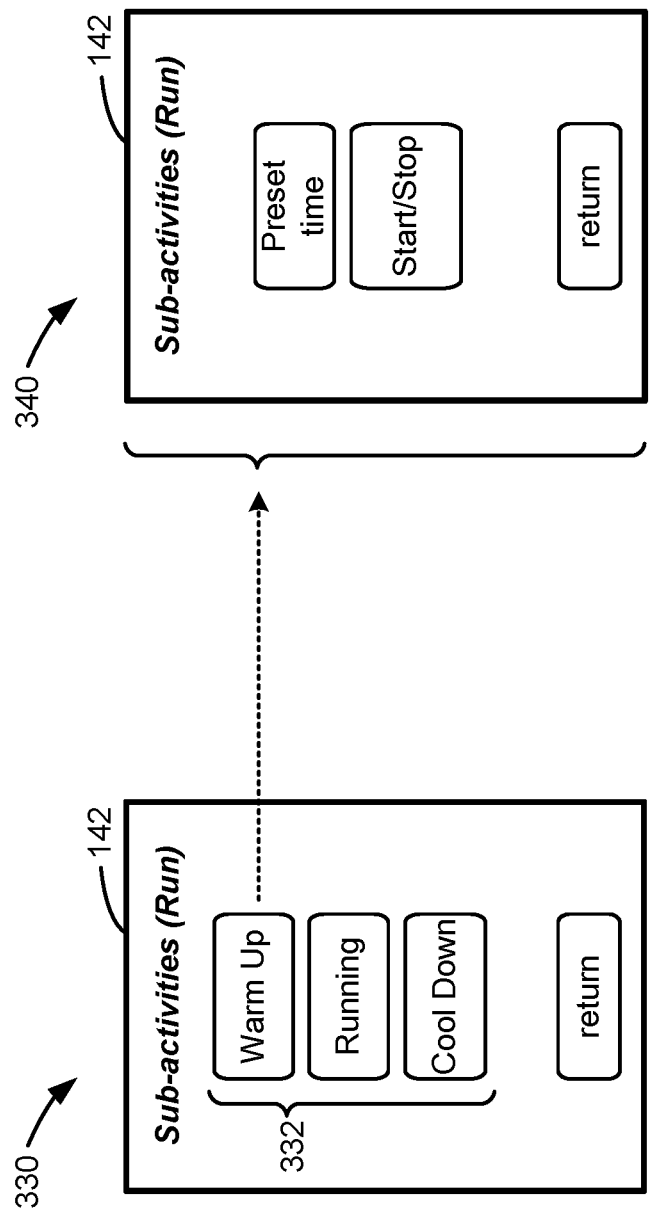

FIG. 8B shows an example of a sub-activity GUI 330 for the activity of running, which may be invoked, for example, by a patient selecting the run learn option 322 (FIG. 8A). Sub-activity GUI 330 provides options 332 for each sub-activity, which selections can be used to inform the MDA 170 when transitions between the sub-activities are taking place or are likely to take place. Thus, when one sub-activity is selected (e.g., warm up), the patient can at GUI 340 enter a preset time as to how long this sub-activity typically takes. Alternatively, the patient can use the start/stop option to inform the MDA 170 as to when the patient has begun and ended the sub-activity—in effect, to time the sub-activity. In either case, the patient performs the activity, or individual sub-activities, and activity learning file(s) 324 is/are created, and with portions being associated with the different sub-activities.

After several iterations of such learning, the patient will eventually be able to select the activity 304 from the activity GUI 300 (FIG. 8A), with the MDA 170 adjusting the stimulation parameters to coincide with each sub-activity. For example, MDA 170 may upon consulting the activity learning file(s) 324 determine an Iopt1 for the warm up sub-activity; Iopt2 for the active running sub-activity; and Iopt3 for the cool down sub-activity.

The MDA 170 can understand the transition between different sub-activities—and hence when Iopt for each sub-activity should be transmitted to the IPG—in different manners. In one example, The MDA 170 may determine transitions based on the anticipated time spent performing each sub-activity. The anticipated sub-activity time may be determined based on historical data, i.e., averaging the time previously spent in each sub-activity as gleaned from the activity learning file(s) 324, or the sub-activity time may be preset by the patient as discussed earlier.

In another example, the MDA 170 may determine a transition from one sub-activity to another as a function of A' and FP' presently being reported from the IPG. For example, if the activity learning file 324 also includes activity parameters (A, FP) (FIG. 8A), the MDA 170 can monitor the currently-reported activity parameters (A', FP'); compare them to the stored activity parameters in the file(s) 324 for each sub-activity to determine a sub-activity having similar values; and automatically change the optimal stimulation (Iopt) accordingly, which again can be different for each sub-activity. In this regard, note that an activity history file 328 can be created from the activity learning file(s) 324 for each sub-activity—i.e., as populated with data I, A, and FP occurring during the particular sub-activity.

Figure 9:
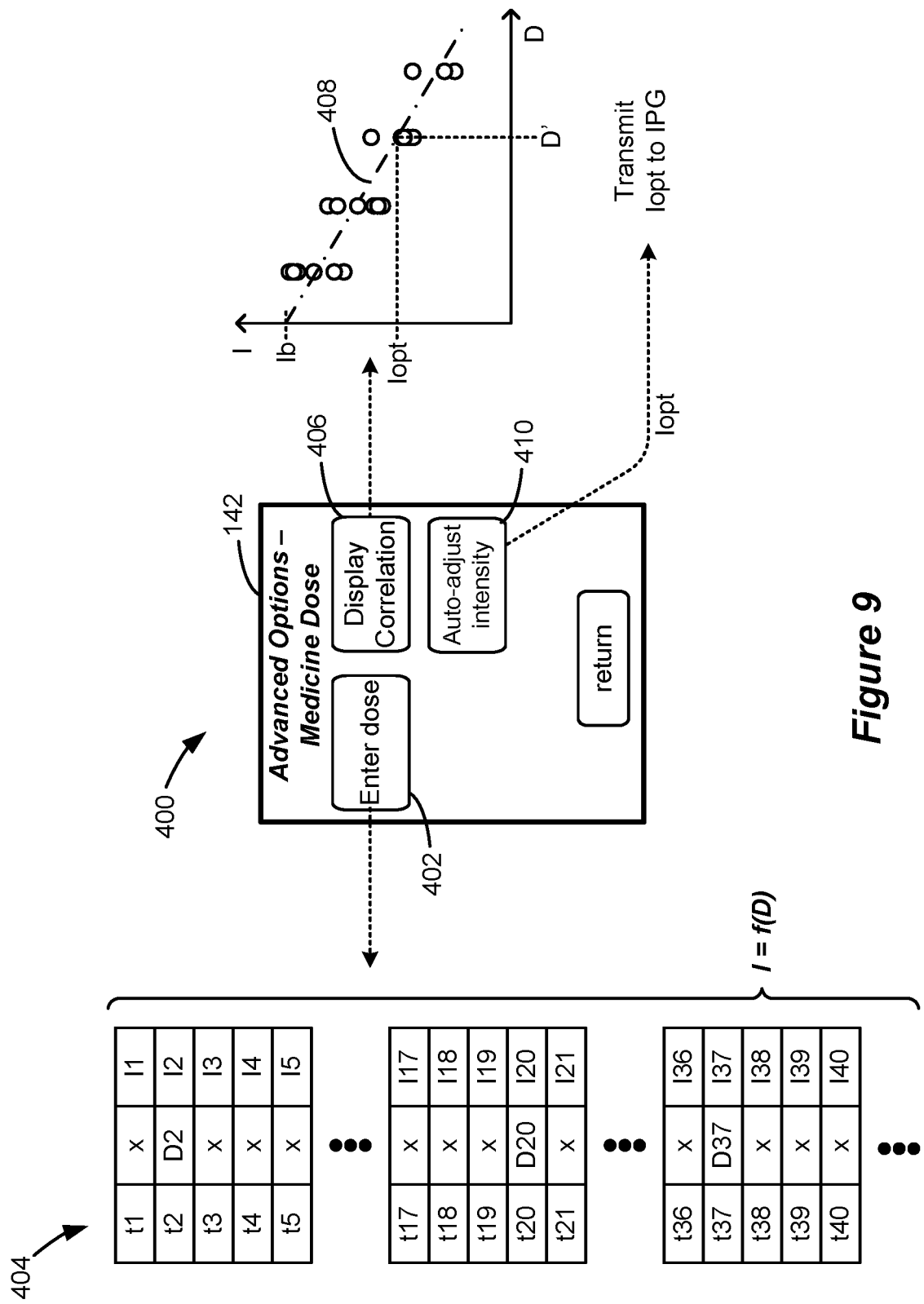
FIG. 9 shows medicine dosing advanced options of the MDA.

FIG. 9 illustrates the GUI 400 that appears in the MDA 170 when the "medicine dose" advanced option 204 (FIG. 6) is selected by the patient. In this regard, patients with IPGs may be experiencing pain (e.g., in an SCS application) and typically have some experience with taking certain medicines, such as analgesics. Patients with IPGs may also experience other symptoms (e.g., tremors in a DBS application) and take other types of medications to alleviate those symptoms as well. An IPG is often intended to supplant the need for such medications, although some IPG patients may still continue to take (preferably reduced) amounts of medications even after receipt of an IPG. Medicine dose advanced option 204 assists patients in understanding the relationship between stimulation therapy and medicinal therapy, and to control the stimulation parameters of the IPG based on patient medicine intake. Again, only control of the stimulation parameter of intensity is discussed for simplicity, even though other stimulation parameters could be controlled as well.

Medicine dose GUI 400 includes an enter dose option 402 to allow a patient to enter a particular dose (D) of a medication taken. A patient would preferably access this option 402 as soon as she takes her medicine, but the dose could be entered later, in which case the patient would also preferably enter the approximate time the medicine was taken. The doses are time stamped (or are associated with a time entered by the patient) and stored in a dosing file 404 by the MDA 170. Also in the dosing file 404 is stimulation intensity (I), which, as before, can be provided by the MDA 170 as the patient uses it to change stimulation, or which can be provided by the IPG log file 250 (IPG data log 220 as transmitted to the external device 140) and later reconciled with the dosing file 404 via the timestamps (t). Note that patients may adjust intensity more frequently than they may take their medicine, and so many of the dose entries in dosing file 404 may be blank.

After a sufficient amount of data is entered into the dosing file 404, the patient can select a display correlation option 406, which uses the dosing file 404 to correlate medicine dose (D) with intensity (I). In this regard, the MDA 170 may correlate I and D in the dosing file 404 (I=f(D)), such as by using linear regression analysis or other known curve-fitting techniques (if a linear relationship is not apparent) to determine a dose-versus-stimulation curve 408, which can be displayed 142 on the external device 140 for the patient.

The MDA 170 may make reasonable assumptions when assessing the data in the dosing file 404 to determine the data points (D, I) to use in establishing this correlation. For example, the MDA 170 may average all values for I appearing after a given dose in the dosing file 404. For instance, intensities I20-I36 may be averaged and associated with dose D20 to create one (D, I) data point upon which the correlation curve 408 is based. Or realizing that a dose may not be therapeutically effective in a patient until after some time, the MDA 170 may instead average slightly-later values for I, and perhaps even those occurring after a next dose D37 (e.g., I22-I38). The MDA 170 may also ignore data in the dosing file 404 that occurs when a dose is changed, because a steady state of the medicine in the patient cannot be assured. For example, if D2=D20=D37=30 mg, and D58=D72=D91=20 mg, I58-I71 may be ignored, or may be associated with a factitious dose of 25 mg between the intervening doses. In any event, curve 408 can be useful to the patient as well as her clinician to understand how well IPG therapy is supplementing or reducing medicinal therapy.

Curve 408 is also useful in forecasting IPG stimulation parameters once IPG therapy overtakes the patient's medicinal therapy. In this regard, it is typical for IPG patients to continue to take their medication after receiving their IPGs, with the dose reduced over time as stimulation is gradually increased. Curve 408 can track how this is progressing, and can provide an estimate for the baseline stimulation parameters (e.g., a baseline intensity Ib) a patient can expect to use in her IPG once she is no longer taking medicine (i.e., when D=0).

Curve 408 can also be used to control the IPG, which is particularly useful for those patients that still require medicinal therapy in addition to IPG therapy. In this regard, a patient can select an auto-adjust intensity option 410. Upon selection of this option 410, the MDA 170 will retrieve the current (last) dose (D') in the dosing file 404, calculate or update the dose-versus-stimulation curve 408 if necessary, select an Iopt corresponding to the current dose D' (using curve 408), and transmit Iopt to the IPG for execution. When determining Iopt, the MDA 170 preferably considers the time stamps in the dosing file 404. For example, if the last entered dose in the dosing file was three days before selection of the auto-adjust intensity option 410, the MDA 170 may assume that the medicine has worn off and that the current dose in the patient is zero despite the last entry in the dosing file, and provide Iopt=Ib to the IPG.

The MDA 170 might also be programmed with other information, such as dose concentration curves (including ramp to peak concentration and elimination half-life) of the patient's medicine, which would allow the MDA 170 to even more accurately deduce the dose-versus-stimulation correlation represented by curve 408, and to more accurately provide Iopt during auto-adjustment. For example, if the MDA 170 understands that the last dose D was taken t hours ago, the MDA 170 may estimate that the patient's current dose level is D' (e.g., less than D), and can then use curve 408 to determine Iopt which is then transmitted to the IPG. As time increases without entry of another dose in the dosing file 404, it would be expected that this assessment would cause Iopt to increase over the time increase.

Figure 10A:
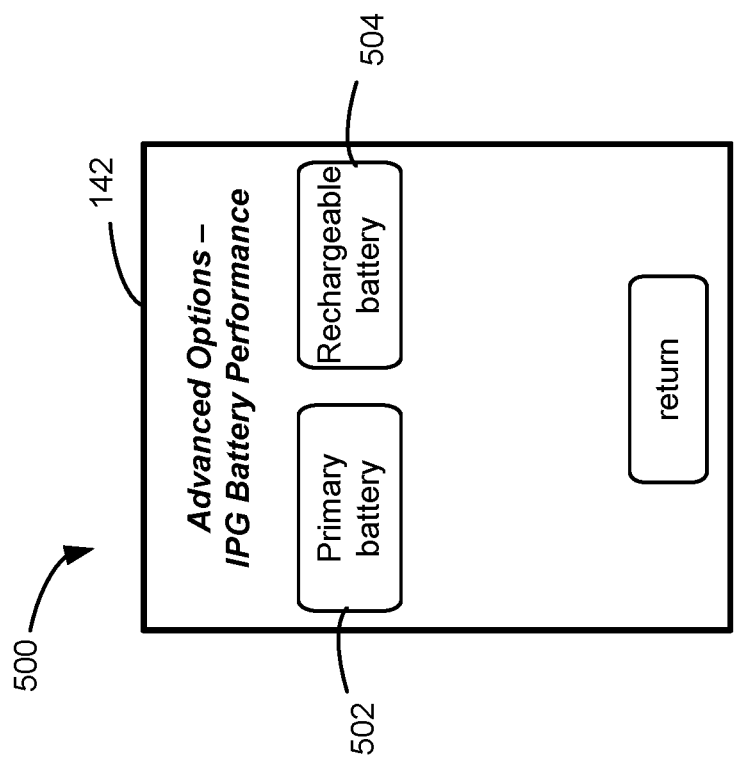
FIGS. 10A-10D show battery performance advanced options of the MDA.

FIG. 10A shows a GUI 500 for the IPG battery performance advanced option 206 provided earlier (FIG. 6). This aspect of MDA 170 can vary depending whether the battery 14 in the IPG is a non-rechargeable primary battery or a battery that is rechargeable (e.g., by the external charger described earlier). Options 502 and 504 for both types of batteries are shown in FIG. 10A. In one implementation, the MDA 170 when initialized on the external device 140 could ask the patient which type of battery 14 is used in his IPG, and subsequently only enable and present the GUI 520 (FIG. 10B) or 540 (FIG. 10C) corresponding to option 502 or 504.

Figure 10B:
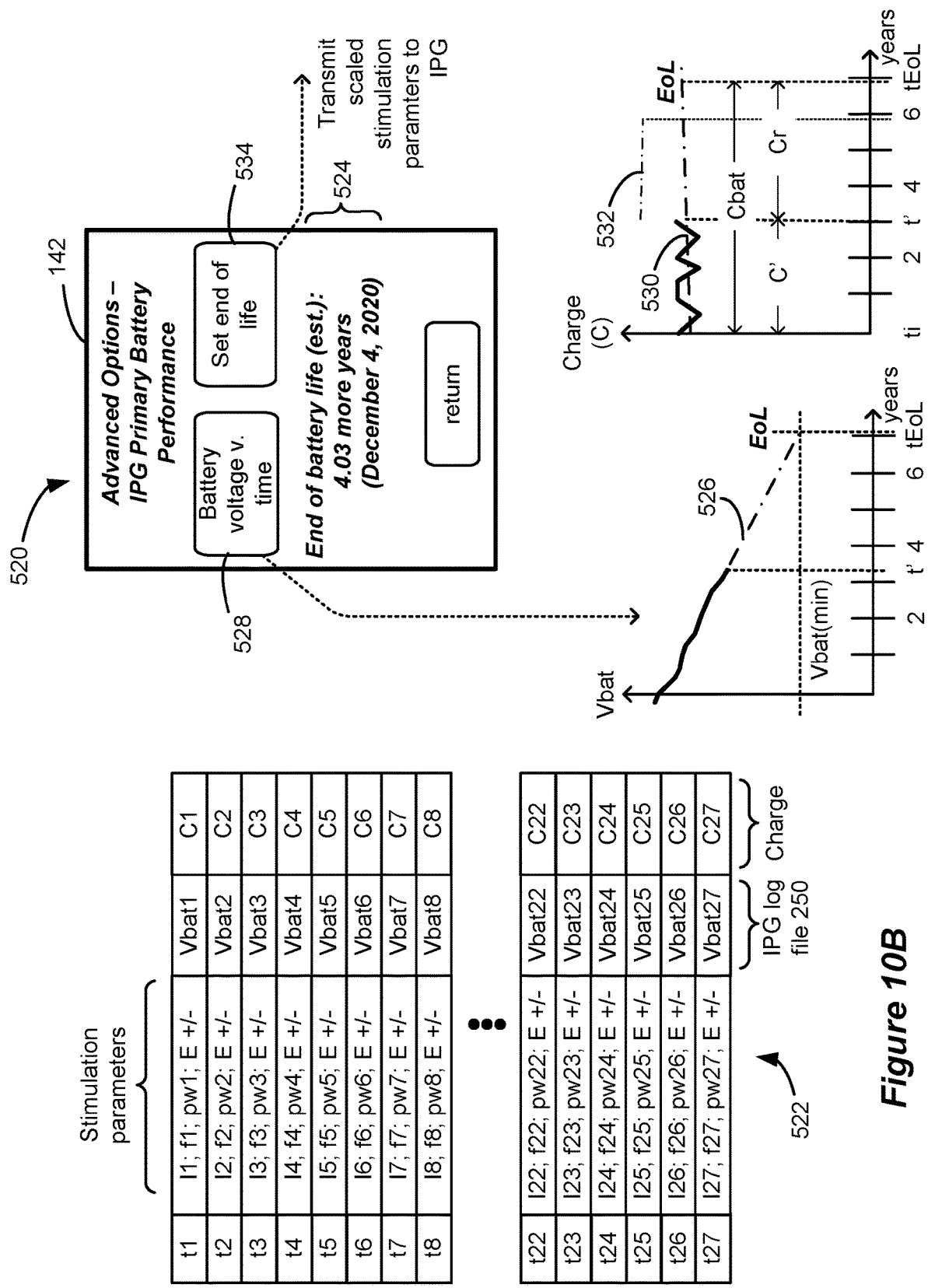

A primary battery performance GUI 520 results from selecting option 502, and is shown in FIG. 10B. Also shown in FIG. 10B is a primary battery history file 522 maintained by the MDA 170, which includes the stimulation parameters (I, f, pw, active electrodes and polarities) and the battery voltage, Vbat, which are time stamped. Vbat is measured at and reported from the IPG (e.g., as part of IPG data log 220), and is preferably accessible to the MDA 170 via IPG file log 250. The stimulation parameters can likewise be reported from the IPG, or already known by the MDA 170. If the stimulation parameters come from the MDA 170, the battery voltages can be reconciled and included in the primary battery history file 522 using the time stamps (t) as discussed previously.

As shown in FIG. 10B, the primary battery performance GUI 520 may immediately notify the patient of certain useful parameters that a patient might wish to review (524), such when the battery 14 is expected to reach the end of its life based on the historical usage data in the primary battery history file 522. This is important, as the patient will need to have his IPG removed and a new IPG implanted at this time. Review of the end of life may also be a selectable option.

The end of life calculation as presented at 524 can be performed by the MDA 170 in several different ways. In a simple way depicted at the bottom of FIG. 10B, the MDA 170 may curve fit Vbat versus time 526 using the data in the primary battery history file, and extrapolate the time from the present (t') when the battery voltage will reach a minimum operational voltage, Vbat(min), for satisfactory IPG operation (tEoL). Viewing a graph of Vbat versus time (on display 142) is also selectable as an option 528, which may include curve 526 as well as the actual historical performance of Vbat. The battery versus time correlation 526 and its extrapolation to determine end of life may not consider the entirety of the data in the primary battery history file 522, but may only include data over a recent time period (e.g., one month) better indicative of the patient's recent current stimulation parameters and hence IPG power draw, which may historically vary.

Because the discharge curves of primary batteries (i.e., Vbat) are non-linear and thus may be difficult to curve fit, the MDA 170 may employ other means to estimate primary battery end of life that considers the stimulation parameters in the primary battery history file 522. For example, the MDA 170 can calculate the charge C expended by battery 14 in the IPG for each entry in the primary battery history file 522. The charge for each therapeutic pulse issued by the IPG comprises the intensity (I) times the pulse width (pw). To determine the total charge expended for each entry in file 522, this per-pulse charge is multiplied by the number of pulses the IPG delivered during the entry, which comprises the frequency (f) times the duration of the entry. For example, note from the primary battery history file 522 that stimulation parameters I3, f3, and pw3 were in effect in the IPG from time t3 to t4. The total charge expended by the battery 14 during this entry is thus: C3=I3*pw3*f3*(t4−t3), which value can be added to the primary battery history file 522 as shown. The number of active electrodes (which may be more than two) may also be relevant to this charge calculation, although it is assumed for simplicity that the intensity I in the primary battery history file 522 comprises the total current provided to the patient by all active electrodes.

The MDA 170 may then curve fit 530 data points (Cx, tx) as set forth in the primary battery history file 522, as shown at the bottom right in FIG. 10B. Curve 530 can be used by the MDA 170 in conjunction with the total capacity of the battery 14 (Cbat) and the total charge expended by the battery to date (C') to estimate the end of life (tEoL) of the primary battery. Battery capacity Cbat, normally expressed in amp-hours, is typically known and thus can be provided or programmed into the MDA 170. The total charge (C') used by the battery 14 up to the present time (t') can be determined either by adding the charge values in the primary battery history file 522 from inception (ti) to present time (t'), or by determining the area under curve 530 between times ti and t'. This allows the charge remaining in the battery (Cr) to be determined (Cr=Cbat−C'). Curve 530 can then be extrapolated, with tEol being determined as the time at which the area under curve 530 from the present (t') equals Cr. Having the primary battery history file 522 also track the cumulative charge used at each entry, or the charge rate, can also be useful in these calculations as one skilled in the art will appreciate, although this is not shown.

Curve 530 need not be curve fit using all historical data in the primary battery history file. Instead, only the patient's current stimulation parameters, or stimulation parameters used recently (e.g., one month), may be used to provide a estimation for tEoL that is consistent with the stimulation parameters being currently or recently used. For example, if the patient is presently using more power-intensive stimulation parameters than he has historically, the end of life calculation will reflect this, as shown in extrapolation 532 in the graph in FIG. 10B.

If the battery 14 it approaching its end of life, the set end of life option 534 provided in the primary battery performance GUI 520 allows the patient the ability to ensure that at least some level of stimulation will be provided by his IPG up to a convenient date. Assume for example on Jan. 1, 2014 that the end of life estimation (tEoL) is 30 days away (Jan. 31, 2014), while the patient is away on business. The patient can use this option 534 to enter a more convenient date, such as one that is 50 days away (Feb. 20, 2014), after the patient has returned. When the patient enters this new date, the MDA 170 will adjust the stimulation parameters accordingly and send them to the IPG.

The MDA 170 can adjust the stimulation parameters by determining the time to the currently-estimated end of life (i.e., 30 days); the time to the desired end of life entered by the patient (i.e., 50 days); and their ratio to determine a scalar (0.6). The MDA 170 can then use this ratio to scale the stimulation parameters accordingly. This may involve just scaling the patient's current intensity setting (I), but pulse width (pw) or frequency (f) could also be scaled, or all three to a slighter degree. Or the MDA 170 could determine average simulation parameters values from the primary battery history file 522, and scale these appropriately and transmit them to the IPG.

The MDA 170 at this point might also allow the patient to choose which stimulation parameters to scale consistent with the scalar calculated, so the patient can try out different stimulation parameters to see what will feel best during this extended period. For example, the MDA might allow the patient to scale the intensity by 0.9, the pulse width by pulse width by 0.8, and the frequency by 0.85, as these scalars when multiplied are approximately equal to the 0.6 scalar computed by the MDA 170, and thus are consistent with the power savings the patient's end of life choice requires.

While such new stimulation parameters may not be optimal for the patient, they would presumably be better than no stimulation at all, and thus allowing the patient to "get by" until they can reach their clinician to discuss receiving an IPG replacement. In light of the importance of these scaled settings, the MDA 170 may not, after use of the set end of life option 534, allow the patient to further use the MDA to change stimulation parameters, or may at least warn the patient that power saving stimulation parameters are in effect before they are changed.

Figure 10C:
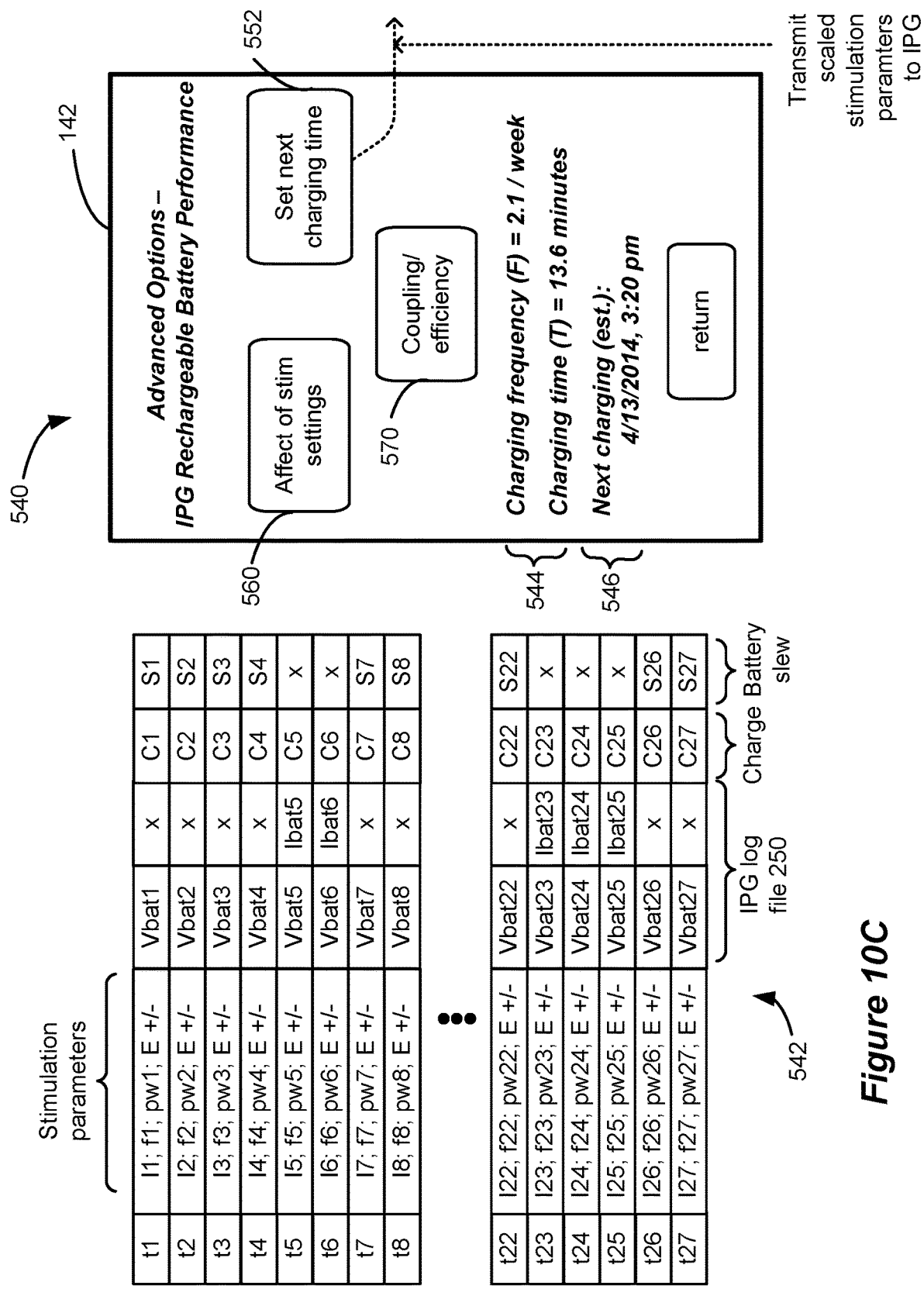

A rechargeable battery performance GUI 540 results from selecting option 504 in the IPG battery performance GUI 500 (FIG. 10A), and is shown in FIG. 10C. Also shown is a rechargeable battery history file 542 maintained by the MDA 170, which includes the stimulation parameters (I, f, pw, active electrodes and polarities), the battery voltage (Vbat), and the battery recharge current (Ibat), which are all time stamped. Vbat and Ibat as noted earlier comprise part of IPG data log 220 (FIG. 7A) as transmitted from the IPG to the external device 140, and would be accessible to the MDA 170 via IPG file log 250. The stimulation parameters can either come from the MDA 170 or from the IPG, similar to the primary battery history file 522 of FIG. 10B.

As shown in FIG. 10C, the rechargeable battery performance GUI 540 may immediately notify the patient of certain useful parameters that a patient might wish to review (544), such as the average charging frequency (F), i.e., the average number of times the IPG battery has been charged by the external charger over some time period, such as a week for example, and the average time (T) of each external charger charging session. These parameters 544 may also comprise selectable options.

The MDA 170 in conjunction with the rechargeable battery history file 544 can calculate the average charging frequency F by averaging the times between subsequent charging sessions, the beginnings of which can be determined by noting where values for T␣␣␣␣are reported in the rechargeable battery history file 542 after pauses. For example, it is seen that a charging session began at time t5 (as T␣␣␣␣is reported after a pause), and that the next charging session began at time t23. As such these charging sessions were separated by a time t23−t5 (say 3.3 days). The time between other subsequent charging sessions can likewise be determined by the MDA 170 (e.g., 3.0 days, 3.7 days, etc.), with the various times averaged (e.g., to determine an average time between charging sessions (e.g., 3.3 days). From this average, a charging session frequency F over a suitable time period (e.g., 2.1 charging sessions/week) can be determined and displayed (544).

The MDA 170 can calculate the average time for charging T by ascertaining the time between when Ibat appears after a pause (t5) and then ceases (t6), i.e., t6−t5. These active charging time periods (t6−t5; t25−t23) can then be averaged to determine T.

When computing the average frequency F and time T (544), the MDA 170 may consider the entirety of the data in the rechargeable battery history file 542, but may also only include data over a recent time period (e.g., one month) better indicative of the patient's recent stimulation parameters and IPG power draw.

Alternatively, when computing the average frequency F and time T (544), the MDA 170 may consider only portions of the primary battery history file 542 that match or are close to the patient's present stimulation settings, which portions would generally have involved power draws in the IPG similar to the patient's current stimulation settings. Specifically, the MDA 170 may consider and use in the F and T calculations only entries in the rechargeable battery history file 544 that match or are close to a charge rate (R; charge/time) currently experienced in the IPG in light of the stimulation parameters. Calculating the charge used at each entry in the rechargeable battery history file 542 (C) (see FIG. 10B) is also helpful here. Thus, the MDA 170 may determine the relevant time periods for the F and T calculation as discussed earlier. The MDA 170 then preferably determines the charge rate R at least during non-charging periods (e.g., the sum of C7 to C22/t22−t7), although charge values during charging periods (e.g., from t5 to t6) could be considered as well. The IMDA 170 then determines and excludes periods in the file 542 have charge rates R that don't match or that aren't close to the patient's current charge rate R', which can be determined by assessing entries in the file after the last charging session (e.g., from t26 forward: (C26+C27)/(t26−t27)). Once these portions of file 542 are excluded, the MDA 170 can then average the remaining relevant time periods as discussed above to determine values for F and T (544) that better match the patient's present stimulation settings.

Calculations for determining F and T at 544 can also involve the battery voltage Vbat in the rechargeable battery history file 542. Vbat will of course drop during periods when the battery 14 is not being charged (e.g., from t7 to t22), and the slew rate (S) at which Vbat is dropping during such periods can be determined (e.g., S8=Vbat8−Vbat9/t9−t8), and added to the rechargeable battery history file 542. While the battery slew rate can be determined for each entry in the file 542, it may also only be necessary to determine a single battery slew rate for each non-charging period. This could occur by determining Vbat at the beginning and ends of each of these periods (e.g., Vbat7 and Vbat22), and dividing their difference over the elapsed time (e.g., S22= (Vbat7−Vbat 22)/(t22−t7)). The MDA 170 could also curve fit the battery voltages (e.g., Vbat7 through Vbat22) with their corresponding time stamps (e.g., t7 through t22), with the slope of this correlation comprising the slew rate for the non-charging period.

Regardless of how battery slew is determined, the MDA 170 can again determine and exclude periods in the file 542 having battery slew rates that don't match or that aren't close to the patient's current battery slew rate S', which again can be determined by assessing the last or most recent entries in the file 542. Once these portions of file 542 are excluded, the MDA 170 can then average the remaining relevant time periods to determine values for F and T (544) that better match the patient's present stimulation settings.

Further refinements to the calculation of F and T (544) can be made by the MDA 170 by considering the magnitude of the battery voltage Vbat. This can be useful because it cannot always be assumed that the battery 14 is at the same low level when charging begins, nor can it be assumed that the battery will always be charged to the same high level when charging ends. Assume for example that Vbat is normally around 4.0V after charging (e.g., at t26) and is normally around 2.0V before charging (e.g., at t22). If a patient used his external charger earlier than necessary in some instance (e.g., when Vbat=3.0V), then the frequency (F) and time (T) associated with that charging session would be unusually short. A patient may also not fully charge the battery (e.g., to Vbat=4.0V), which again would render values for F and T that would be shorter than normal. Accordingly, the MDA 170 may assess Vbat for unusual values in the rechargeable battery history file 544, and exclude portions of the file 542 associated with those voltages from the average F and T calculations displayed at 544. This assessment may exclude portions where Vbat is too high or too low at the beginning of charging, or too high or too low at the end of charging, or where the difference between Vbat at the beginning and end of charging is too low or too high.

Figure 10D:
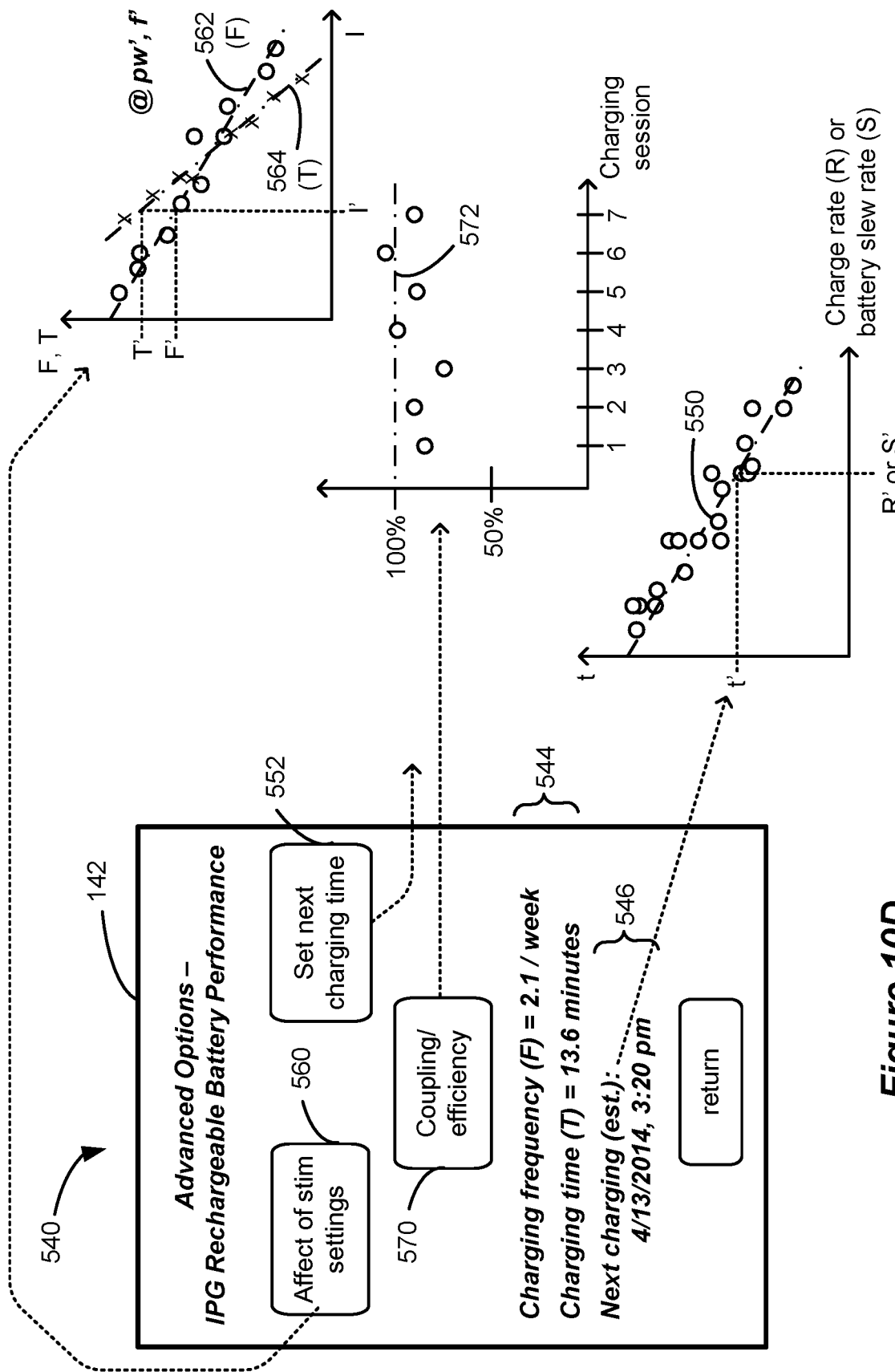

The estimated time to a next charging session is also displayed at 546. As shown in FIG. 10D, this also can be calculated by the MDA 170, and calculating the charge rate (R) or battery slew rate (S) can also be helpful here. The MDA 170 can determine such rates for each non-charging period, as well as the duration t of those periods (e.g., t22−t7), thus arriving at a number of data points (R,t) or (S,t). The MDA 170 can curve fit these data points (550), as shown in the graph at the bottom of FIG. 10D. Portions of the data reflecting unusual values for Vbat may be excluded when determining such correlations as discussed above.

The MDA 170 can then consider the charge rate or slew rate R' or S' currently being used by the patient's IPG, and using curve 550, determine the time between charging for such settings (t'). Calculating the next time at which the IPG will need to be charged (546) then requires the MDA 170 to review the rechargeable battery history file 542 to determine when the IPG was last charged (e.g., t25); to determine the current time (e.g., t34); to determine how far the patient is into time period t' (i.e., t34–t25); and to subtract this value from t', which can be displayed at 546.

Further refinements to the next charging time estimation (546) can be made by the MDA 170 by considering the magnitude of the battery voltage, Vbat. For example, curve fitting in each non-charging period can extrapolate or interpolate when the charge rate or battery slew rate during each of these periods would have crossed known optimal high and low threshold values for the battery (e.g., 4.0V and 2.0V), even if they didn't actually do so. These extrapolated or interpolated times can then determine a duration for each non-charging period (which may differ from the true duration of the non-charging period). These modified t values may then be included with the data points (R,t) or (S,t), which are curve fit (550) and which therefore may lead to more accurate correlations.

In another refinement to the next charging time estimation (546), the present value of the battery voltage Vbat (Vbat') and/or the value for Vbat after the last charging period (e.g., Vbat26) may be considered. This can be important because the above method for time estimation using a charge rate or battery slew rate may assume that the battery is always charged to a known level (e.g., 4.0V), when the reality is different. Assume for example that the correlation 550 is premised on the assumption that the battery is charged to 4.0V, and that current voltage of the battery should be 3.2V. If the rechargeable battery history file 542 shows that the battery had actually last been charged to 4.2V, and that the battery is currently at 3.4V, then the next charging time estimation (546) can be lengthened accordingly. This is easiest to understand using the context of the current battery slew rate S': if there is a difference of 0.2V in assumed and actual values as in the present example, this difference can be divided by the slew rate S' to determine an additional time to add to t' to render a more accurate next charging time estimation (546).

If a patient won't be able to charge his PG battery before the estimated next charging time (546) (because the patient has left his external charger at home on a business trip for example), the set next charging time option 552 can be used. Similar to the set end of life option 534 for the primary battery (FIG. 10B), the set next charging time option 552 will allow a patient to input a convenient time for a next recharging, and the MDA 170 will scale the stimulation parameters accordingly and transmit them to the IPG to reduce power consumption in the IPG. This process may be essentially the same as described earlier for the primary battery in that it involves calculating a scalar based on the current time estimated to a next charge using the patient's current stimulation settings (in 546), and the new time entered by the patient in option 552. As with option 534, option 552 might involve automatically scaling one or more stimulation parameters consistent with the calculated scalar, or allow the patient to scale them consistent with the calculated scalar. Also similar to option 534, the MDA 170 may not allow the patient to further use the MDA to change stimulation parameters, or may at least warn the patient that power saving stimulation parameters are in effect.

The rechargeable battery performance GUI 540 may also provide options 560 and 570 to allow a patient to review other aspects of charging. Option 560 for example allows the patient to review the effect of stimulation settings on charging performance, which information may be displayed graphically, and which may for example focus on intensity, the stimulation parameter that the patient is most likely to modify with the MDA 170. As shown in FIG. 10D, option 560 might for example display graphs showing the effect of intensity (I) on both charging frequency (F) (562) and time of charging (564) (T), such as are reported at 544.

To determine these correlations, the MDA 170 may disregard entries in the rechargeable battery history file 542 that do not match the patient's other current stimulation parameters (e.g., pulse width pw' and frequency f), or may choose to process only entries having pulse widths or frequencies that have been consistently used by the patient as reflected in file 542. Or the MDA 170 may allow the patient to review the correlations 562 and 564 based on a selected pulse width and frequency, and then disregard non-matching entries. With certain entries in the rechargeable battery history file 542 disregarded in these manners, the MDA 170 can determine remaining non-recharge periods in rechargeable battery history file 542 consistent with pw', f (e.g., t7-t22); average the intensities during these periods; calculate F during these periods to arrive at data points (I, F); and calculate T after these periods to arrive at data points (I, T). These data points can then be curve fit to correlate them, which correlations can be displayed 562 and 564 for the patient as shown. Current estimations for F' and T' may also be shown for the intensity value for patient is currently using (I'), which may also comprise the average charging frequency (F) and time (T) appearing at 544.

The coupling/efficiency option 570 allows the patient to see how efficient various charging sessions have been, e.g., how well the external charger has been coupled to the charging coil 32 in the IPG. Poor coupling results in poor charging efficiency and weak charging of the battery 14, and can result from the external charger being misaligned with the IPG. See, e.g., U.S. Patent Application Publication 2013/0096652. Thus, the patient can review data presented at this option 570 to understand if he can be more attentive to aligning the external charger during a charging session to more quickly charge the battery. In this regard, it is useful for the MDA 170 to have an established baseline 572 indicative of good coupling, which is represented as 100% in the depicted graph. This 100% value can represent the battery charge current Ibat that results during an initialization or test period in which the external charger is carefully placed directly over the center of the IPG, at which point the external charger is turned on to generate a magnetic charging field. The MDA 170 may prompt the patient to perform these initialization or test steps upon first executing the MDA 170 at the external device 140. Providing a patient-specific baseline 572 in this manner is useful, because different patients will have their IPGs implanted at different depths and orientations, and so a good, efficient value for Ibat will vary from patient to patient.

Once this coupling baseline has been determined and stored with the MDA 170, the MDA can thereafter review the rechargeable battery history file 544 to determine when charging sessions have occurred (e.g., t5 to t6; t23 to 25, etc.), and average the values for Ibat during these periods. These Ibat values can then be ratioed with the baseline 572 to determine the displayed percentages. Notice for example that charging current Ibat as measured by the IPG during the third charging session is about 75% of Ibat measured during initialization or test. The patient would conclude from this that the coupling between the external charger and the IPG had been relatively poor during this charging session.

While reference has been made to various files (324, 328, 404, 522, 542) in explaining operation of the MDA 170, it should be understood that these files may represent subsets or supplementation to the IPG log file 250, and so such files may either be stored in association with the IPG log file 250, or could simply comprise different portions of the log file 250. It has nonetheless been convenient to discuss such files separately so that only relevant portions of the IPG log file 250 are shown to explain different features of the MDA 170. Such files, like IPG log file 250, may also be stored in memory 232 (FIG. 7B), and hence also accessible to and populatable by the MDA 170.

One skilled in the art will understand that the disclosed medical device application will comprise instructions that can be stored on non-transitory machine-readable media, such as magnetic, optical, or solid-state discs, integrated circuits, tapes, etc., and which can be executed on the external device. Examples of likely storage devices having machine-readable media which would store the disclosed medical device application include the external device (e.g., after it is downloaded, on its hard drive), or an Internet or other network server, such as an implantable medical device manufacturer's server or an app store server, which a patient can access to download the medical device application to his external device as noted previously. However, other storage devices could include disks, memory sticks or modules, which may be portable or which may be integrated within other computers or computer systems.

Control circuitries operable in the IPG and external device can comprise a microcontroller, microprocessor, or other logic circuitries (e.g., FPGAs) capable of executing the medical device application as disclosed herein. Such control circuitries can in one example comprise a Part No. MSP430 microcontroller manufactured Texas Instruments, Inc., as described in the data sheet submitted with the Information Disclosure Statement included herewith, which data sheet is incorporated herein by reference in its entirety.

Although various Graphical User Interfaces (GUIs) were disclosed separately for ease of illustration and discussion, one skilled will understand that these GUIs all constitute portions of the GUI for the MDA.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for using an external controller for an implantable stimulator device, wherein the implantable stimulator device comprises a rechargeable battery, the method comprising:
   providing a user interface on the external controller to allow a patient to program the implantable stimulator device with a stimulation program;
   storing at the external controller information indicative of one or more of charging or use of the rechargeable battery in the implantable stimulator device;
   estimating at the external controller from the stimulation program and the information a charging frequency and a charging duration for the rechargeable battery, wherein the charging frequency indicates how often future charging sessions should occur and wherein the charging duration is indicative of an expected duration of the future charging sessions; and
   displaying the charging frequency and the charging duration on the user interface.

2. The method of claim 1, wherein the information is received at the external controller from the implantable stimulation device.

3. The method of claim 1, wherein the information comprises information indicative of charging of the rechargeable battery.

4. The method of claim 3, wherein the information indicative of charging of the rechargeable battery comprises one or more of a battery charging current of the rechargeable battery, a charge of the rechargeable battery, or a voltage of the rechargeable battery.

5. The method of claim 4, wherein the battery charging current of the rechargeable battery, the charge of the rechargeable battery, or the voltage of the rechargeable battery are time stamped.

6. The method of claim 1, wherein the information comprises information indicative of use of the rechargeable battery to provide stimulation to the patient.

7. The method of claim 6, wherein the information indicative of use of the rechargeable battery comprises one or more of a stimulation amplitude, a stimulation pulse width, a stimulation frequency, a voltage of the rechargeable battery, or a slew rate of the rechargeable battery.

8. The method of claim 7, wherein the stimulation amplitude, the stimulation pulse width, the stimulation frequency, the voltage of the rechargeable battery, or the slew rate of the rechargeable battery are time stamped.

* * * * *